(12) United States Patent
Yuki et al.

(10) Patent No.: US 8,440,879 B2
(45) Date of Patent: May 14, 2013

(54) FLAVONOID-3',5'-HYDROXYLASE GENE OF COMMELINA COMMUNIS

(75) Inventors: Shunji Yuki, Kusatsu (JP); Satoshi Araki, Katsatsu (JP); Takanori Suzuki, Kasatsu (JP)

(73) Assignee: Ishihara Sangyo Kaisha, Ltd., Osaka (JP)

( * ) Notice: Subject to any disclaimer, the term of this patent is extended or adjusted under 35 U.S.C. 154(b) by 477 days.

(21) Appl. No.: 12/530,497

(22) PCT Filed: Mar. 13, 2008

(86) PCT No.: PCT/JP2008/054653
§ 371 (c)(1),
(2), (4) Date: Sep. 9, 2009

(87) PCT Pub. No.: WO2008/111650
PCT Pub. Date: Sep. 18, 2008

(65) Prior Publication Data
US 2011/0191907 A1 Aug. 4, 2011

(30) Foreign Application Priority Data

Mar. 15, 2007 (JP) ................................ 2007-066539

(51) Int. Cl.
*C12N 15/29* (2006.01)
*C12N 15/82* (2006.01)
*C12N 5/10* (2006.01)
*A01H 5/00* (2006.01)

(52) U.S. Cl.
USPC ........ 800/282; 800/323; 536/23.6; 435/320.1

(58) Field of Classification Search .................. 800/282, 800/317.3, 323, 323.1; 435/320.1, 414, 419
See application file for complete search history.

(56) References Cited

U.S. PATENT DOCUMENTS

| | | | |
|---|---|---|---|
| 6,080,920 A | 6/2000 | Holton | |
| 6,114,601 A * | 9/2000 | Kikuchi et al. | 800/282 |
| PP13,092 P2 | 10/2002 | Glancy | |
| 6,465,630 B1 | 10/2002 | Choi et al. | |
| 6,570,064 B1 * | 5/2003 | Allen et al. | 800/278 |
| 6,660,908 B2 * | 12/2003 | Choi et al. | 800/282 |
| 6,774,285 B1 | 8/2004 | Brugliera et al. | |
| 7,612,257 B2 | 11/2009 | Brugliera et al. | |
| 2002/0120954 A1 | 8/2002 | Choi et al. | |
| 2002/0120959 A1 | 8/2002 | Choi et al. | |
| 2007/0033674 A1 | 2/2007 | Brugliera et al. | |
| 2010/0107277 A1 | 4/2010 | Brugliera et al. | |
| 2011/0126320 A1 | 5/2011 | Tanaka et al. | |

FOREIGN PATENT DOCUMENTS

| | | | |
|---|---|---|---|
| EP | 1 182 257 | | 2/2002 |
| EP | 1 652 916 A1 | | 5/2006 |
| EP | 2143322 | * | 4/2008 |
| JP | 11-505116 | | 5/1999 |
| JP | 2006-512057 | | 4/2006 |
| JP | 2007116396 | * | 4/2007 |
| WO | 96/36716 | | 11/1996 |
| WO | 97/32023 | | 9/1997 |
| WO | 2004/020637 | | 3/2004 |
| WO | 2005/017147 | | 2/2005 |

OTHER PUBLICATIONS

Tanaka et al. Genetic engineering in floriculture, 2005, Plant Cell, Tissue and Organ Culture 80:1-24.*
Su and Hsu, Cloning and expression of a putative cytochrome P450 gene that influences the colour of Phalaenopsis flowers, 2003, Biotechnology Letters 25:1933-1939.*
Halpin et al., Enabling technologies for manipulating multiple genes on complex pathways, 2001, Plant Molecular Biology 47:295-310.*
Tanaka et al. Molecular and Biochemical Characterization of Three Anthocyanin Synthetic Enzymes from *Gentiana triflora*, 1996, Plant Cell Physiol. 37:711-716.*
Davies et al. (2007) ISHS Acta Hort. 755: 171-180.*
Su and Hsu, Biotechnology Letters, vol. 25, p. 1933-1939, 2003.
Nakatsuka et al., Plant Sci., vol. 168, p. 1309-1318, 2005.
Seitz et al., Plant Moi. Biol., vol. 61, p. 365-381, 2006.
Johnson et al., Plant J., vol. 19, No. 1, p. 81-85, 1999.
Fukui et al., Phytochemistry, vol. 63, p. 15-23, 2003.
Altschul et al., Nucleic Acids Res., vol. 25, No. 17, p. 3389-3402, 1997.
Tokuhara and Mii, Plant Cell Reports, vol. 13, p. 7-11, 1993.
Hohn et al., "Cauliflower Mosaic Virus on Its Way to Becoming a Useful Plant Vector" Current Topics in Microbiology and Immunology, vol. 96, p. 194-236, 1982.
Gallie et al., Nucleic Acids Res., vol. 15, No. 8, p. 3257-3273, 1987.
Leon et al., Plant Physiology, vol. 95, p. 968-972, 1991.
Belarmino and Mii, Plant Cell Reports, vol. 19, p. 435-442, 2000.
Mishiba et al., Plant Cell Reports, vol. 24, p. 297-303, 2005.
Kobayashi et al., Science, vol. 286, p. 1960-1962, 1999.
International Search Report for PCT/JP2008/054653, mailed May 20, 2008.
International Preliminary Report on Patentability for PCT/JP2008/054653, mailed Oct. 8, 2009.
Yu et al., "Flavonoid Compounds in Flowers: Genetics and Biochemistry", Internet Citation, Jan. 1, 2006, pp. 282-292, XP007913213, Retrieved from the Internet: URL:http://www.danforthcenter.org/yu/pdf/e-flower-2006.pdf.

(Continued)

*Primary Examiner* — David T Fox
*Assistant Examiner* — Steven Bernacki
(74) *Attorney, Agent, or Firm* — Greenblum & Bernstein, P.L.C.

(57) ABSTRACT

To provide a highly expressed F3'5'H gene, whereby a blue moth orchid can be produced and a method using the gene for producing Orchids having blue flowers.
A gene encoding a flavonoid 3',5'-hydroxylase of *Commelina communis*, which has an amino acid sequence depicted in SEQ ID No: 2 or an amino acid sequence having at least 90% of homology to the amino acid sequence depicted in SEQ ID No: 2. A method for producing an orchid having a blue flower, which comprises transfecting a white moth orchid with the gene, a gene encoding a dihydroflavonol 4-reductase of *Torenia* or *Gerbera*; a gene encoding a flavanone 3-hydroxylase; and a gene encoding an anthocyanidin synthase and expressing the genes.

9 Claims, 6 Drawing Sheets

OTHER PUBLICATIONS

Holton et al., "Genetics and biochemistry of anthocyanin biosynthesis" Plant Cell. American Society of Plant Physiologists, Rockville. MD, US LNKD-DOI:10.1105/TPC.7.7.1071, vol. 7, No. 7, Jan. 1, 1955, pp. 1071-1083, XP002406599, ISSN: 1040-4651.

Wang et al., "Flavonoid-3',5'—hydroxylase from Phalaenopsis: A Novel Member of Cytochrome P450s. its cDNA Cloning, Endogenous Expression and Molecular Modeling", Biotechnology Letters. Kluwer Academic Publishers. DO LNKD-DOI:10.1007/S10529-005-5718-6, vol. 28, No. 5, Mar. 1, 2006, pp. 327-334. XP019231219, ISSN: 1573-6776.

Extended European Search Report that issued with respect to European Patent Application No. 08752160.5, dated Jul. 6, 2010.

Extended European Search Report that issued with respect to European Patent Application No. 08722057.0, dated Jul. 14, 2010.

Hieber et al., Planta, vol. 223, No. 3, p. 521-531, 2005.

Suzuki et al., Biotechnology & Biotechnological Equipment, vol. 14, No. 2, p. 56-62, 2000.

Kim et al., Plant Science, vol. 165, No. 2, p. 403-413, 2003.

International Search Report for PCT/JP2008/058126, mailed Jun. 24, 2008.

International Preliminary Report on Patentability for PCT/JP2008/058126, mailed Nov. 19, 2009.

U.S. Appl. No. 12/596,739 to Satoshi Araki et al., entitled "A Method for Production of Moth Orchid Having Modified Flower Color", which is the National Stage of PCT/JP2008/058126, filed Apr. 25, 2008.

* cited by examiner

FLAVONOID-3',5'-HYDROXYLASE GENE OF COMMELINA COMMUNIS

TECHNICAL FIELD

The present invention relates to a method for producing a plant having a blue flower color by employing the gene recombination technology. Particularly, the present invention relates to a method for producing Orchids having a blue flower color by using a gene encoding a flavonoid-3',5'-hydroxylase (F3'5'H) which is one of enzymes of *Commelina Communis* for synthesizing pigments.

BACKGROUND ART

The color of flower is a particularly important character in ornamental plants, and flowers having various colors have been produced by cross breeding heretofore. However, in the case of the cross breeding, gene sources are limited to species which are capable of cross breeding, and colors to be changed are limited. Further, in a case where only a specific character such as flower color is introduced into a specific variety, it is necessary to repeat backcrossing for long generations, and a lot of effort and time are required. Further, a period of cross breeding varies depending on plant species, and some plants take from a few years to a few decades for blossom. Particularly, Orchids such as moth orchid and cymbidium require a long time for blossom, and it takes a long time to develop such plants. Therefore, although demanded in markets, a superior new variety of moth orchid or cymbidium having a new flower color, particularly blue flower, has not been produced.

In recent years, it is possible to carry out cross breeding over species or genus by the recombinant DNA technology, and it is expected to produce a new variety having a color which cannot be obtained by the conventional cross breeding.

The color of flower derives mainly from three types of pigments: anthocyanin, carotenoid and betalain. Among them, anthocyanin (from orange to blue color) having the broadest maximum absorption wavelength has a role to govern blue color. Anthocyanin is one of flavonoids and biologically synthesized through a metabolic pathway shown in FIG. 1. The color of anthocyanin substantially depends on its chemical structure, and the more the number of hydroxyl groups in a benzene ring is, the more the color becomes blue. The hydroxylation of the benzene ring is catalyzed by a flavonoid 3'-hydroxylase (F3'H) and a flavonoid 3',5'-hydroxylase (F3'5'H). In a case where there is neither F3'H activity nor F3'5'H activity in petal cells, pelargonidin (from orange color to red color) is synthesized, and in a case where there is F3'H activity, cyanidin (from red to crimson color) is synthesized. Further, in a case where there is F3'5'H activity, delphinidin (blue color) is synthesized. Therefore, in order to produce the blue flower color, the role of F3'5'H is considered to be important.

From such a viewpoint, a study is in progress to produce a plant having a blue flower by the gene recombination using F3'5'H.

As conventionally known genes encoding the F3'5'H, genes derived from plants such as *Campanula medium, Catharanthus roseus, Petunia, Eustoma grandiflorum, Nierembergia* sp., *Verbena, Gentiana, Gossypium hirsutum, Lycianthes rantonnei, Solanum tuberosum* and *Torenia*, have been known, however, a gene encoding the F3'5'H which is isolated from a *Commelina communis* has not been reported.

As examples wherein a flower color is changed by using a conventionally known gene, a method for producing a blue carnation by transfecting a carnation DFR (dihydroflavonol 4-reductase) deficient variety with a F3'5'H gene and DFR gene which are derived from *Petunia* (Patent Document 1) and a method for producing a blue rose by transfecting a rose of which internal metabolism pathway is suppressed, with a F3'5'H gene derived from *Viola×wittrockiana* (Patent Document 2) have been reported.

On the other hand, it has been reported to change the flower color of moth orchid by overexpressing an endogenous gene, however, a blue moth orchid has not been produced (Non-Patent Document 1). Further, it has not been reported to have produced a blue variety of cymbidium.

Patent Document 1: WO1996/036716
Patent Document 2: WO2005/017147
Non-Patent Document 1: Su and Hsu, Biotechnology Letters (2003) 25: 1933-1939.

DISCLOSURE OF THE INVENTION

Object to be Accomplished by the Invention

In order to produce a blue flower, the F3'5'H is known to play an important role, and a F3'5'H gene which can be expressed more strongly has been desired.

It is an object of the present invention to find out a highly expressed type F3'5'H gene, whereby blue moth orchid can be produced, and to produce Orchids having a blue flower by using such a highly expressed type F3'5'H gene.

Means to Accomplish the Object

The present inventors have conducted an extensive study in order to accomplish the above object, and as a result they have found that a F3'5'H gene which is derived from *Commelina communis* has a higher effect than that of conventional genes, and that by transfecting moth orchid with the above gene, the color of its flower can be changed to blue. Thus, the present invention has been accomplished.

That is, the present invention relates to a gene encoding a flavonoid 3',5'-hydroxylase of *Commelina communis*, which comprises an amino acid sequence depicted in SEQ ID No: 2 or an amino acid sequence having at least 90% of homology to the amino acid sequence depicted in SEQ ID No: 2.

Further, the present invention relates to a vector, which contains the above gene.

Further, the present invention relates to a method for producing a flower color-changed plant, which comprises transfecting a plant with the above gene and expressing the gene.

Further, the present invention relates to a method for producing a flower color-changed plant, which comprises transfecting an Orchid with the above gene and a gene encoding a dihydroflavonol 4-reductase of *Torenia* or *Gerbera* and expressing the genes.

Further, the present invention relates to a method for producing an Orchid having a blue flower, which comprises transfecting an Orchid having a white flower with the above gene; a gene encoding a dihydroflavonol 4-reductase of *Torenia* or *Gerbera*; a gene encoding a flavanone 3-hydroxylase; and a gene encoding an anthocyanidin synthase and expressing the genes.

Further, the present invention relates to a flower color-changed plant, which is produced by the above method, a progeny having the same characters as the changed flower color; or its tissue.

Further, in the present invention, "flavonoid 3',5'-hydroxylase" (F3'5'H) is an enzyme which catalyzes a reaction to produce dihydromyricetin from dihydrokaempferol. Further, "flavanone 3-hydroxylase" (F3H) is an enzyme which catalyzes a reaction to produce dihydrokaempferol from naringenin. "Dihydroflavonol 4-reductase" (DFR) is an enzyme which catalyzes a reaction to produce leucodelphinidin from dihydromyricetin. "Anthocyanidin Synthase" (ANS) is an enzyme which catalyzes a reaction to produce delphinidin from leucodelphinidin.

Effect of the Present Invention

By using the F3'5'H gene derived from *Commelina communis*, plants having various blue flower colors can be produced. Particularly, by the present invention, it is possible to produce Orchids having blue flower colors which cannot be accomplished by the conventional cross breeding methods.

BEST MODES FOR CARRYING OUT THE INVENTION

Figure 1:
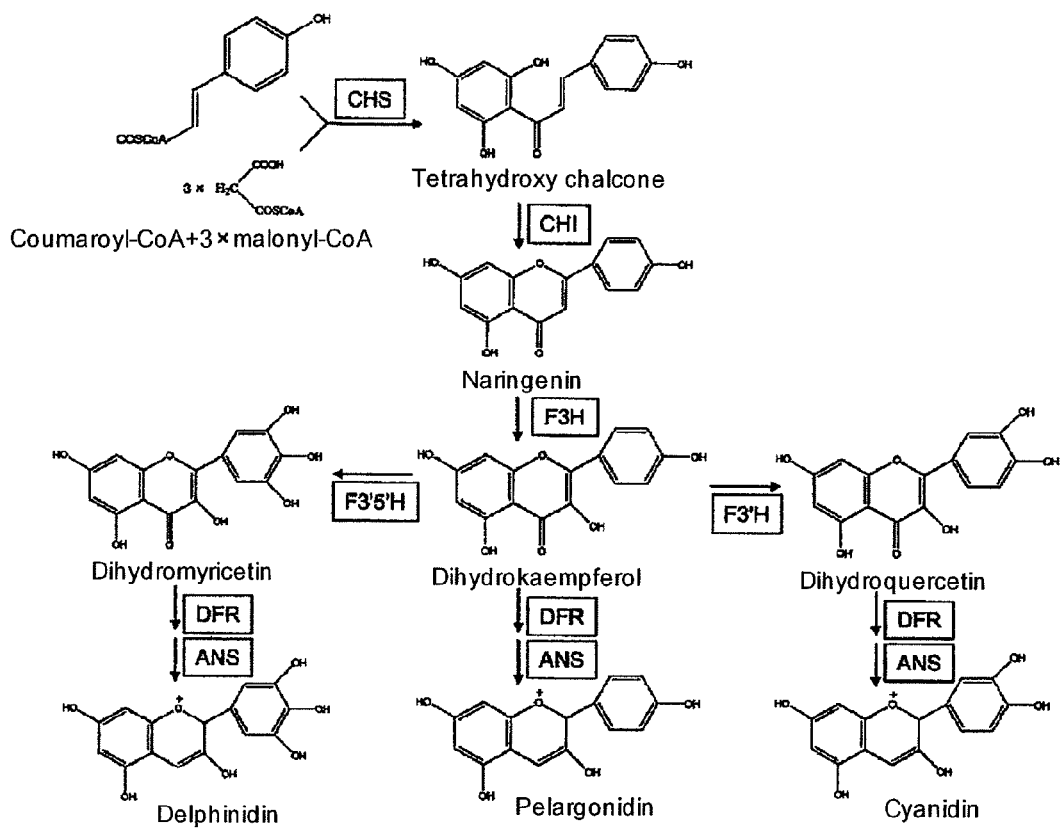
FIG. 1 is a synthetic pathway of anthocyanin.

Now, the present invention will be described in detail, and by these descriptions, other objects, characteristics and superiorities of the present invention will become apparent for those skills in the art. Further, the descriptions of the present specification including the following explanations, specific examples, etc. show preferred embodiments, and those skilled in the art can make various changes and/or modifications (or alternations) of the invention within the concept and the scope of the present invention disclosed in the present specification. Further, all Patent Documents and references cited in the present specification are cited for the purpose of explanation, and it should be understood that their contents are included as a part of the present specification.

By paying attention to a F3'5'H gene which relates to a blue pigment (delphinidin), the present inventors have transfected moth orchid with a known F3'5'H gene which is derived from petunia and has shown practical results in carnation, in order to produce blue orchids. However, the desired effect cannot be obtained. Thus, the present inventors have carried out cloning of F3'5'H genes of various plants in order to find a superior gene. As a result, they have found that a gene (sequence number: 1) derived from *Commelina communis* has a remarkably high pigment production performance. In a case where a petal cell of moth orchid is transfected with the above gene, five times of delphinidin is produced, as compared to the gene derived from petunia which is the prior art. Further, in a case where a petal cell of a red moth orchid is transfected with the gene of the present invention, the flower color is changed to blue tone purple.

Further, it has been found that the flower color is changed from white to blue by transfecting a petal cell of a white moth orchid with the F3H gene which catalyzes an up stream reaction than the F3'5'H and a DFR gene and an ANS gene which catalyze a down stream reaction than the F3'5'H in the synthesis pathway of anthocyanin, in addition to the above F3'5'H gene. Particularly, in a case where a DFR gene derived from *Gerbera* or *Torenia* is used, a flower has a deeper blue color.

The gene derived from *Commelina communis* which is found in the present invention is superior to conventional genes, and by employing the gene of present invention, it is possible to produce a blue type moth orchid. Further, the superiority of the gene of the present invention has been proven on cymbidium as well as on moth orchid, and it has been found that the gene of the present invention can be applied for changing flower colors of various flowering plants.

The F3'5'H gene is isolated from the genome DNA of Asiatic dayflower (nomenclature: *Commelina communis*) or cDNA reversetranscribed from a mRNA transcribed from the above genome DNA. The F3'5'H gene of the present invention is a gene depicted in SEQ ID NO.: 1 encoding a protein depicted in SEQ ID NO.: 2. The gene of the present invention includes genes having a high homology to the above gene, so long as such genes have the F3'5'H enzyme activity. The high homology may be at least 85% homology to the amino acid sequence depicted in SEQ ID NO.: 2, preferably at least 90%, more preferably at least 95%, further preferably at least 98%.

As the flavanone 3-hydroxylase (F3H) gene, the dihydroflavonol 4-reductase (DFR) gene and the anthocyanidin synthetic enzyme (ANS) gene, novel or conventional genes may be used. Specifically, the F3H gene may, for example, be a gene registered on GenBank (accession number: DQ394303, AY221246, AJ493133, AY641730, AF184270, AB078956, AB201760, AY669324, AF036093, AB211958, AB187027 or AB234905). The DFR gene may, for example, be a gene registered on GenBank (accession number: AAB62873, AAC17843, AAD49343, AAQ83576, AAU93766, AAY32600, AAY32601, AAY32602, BAB40789 or BAE79202). The ANS gene may, for example, be a gene registered on GenBank (accession number: AY585677, AY228485, AF015885, AY581048, U82432, AY695817, AB208689, AY997840, AY382828, AY256380, AF026058, Y07955, AF384050, AB097216, AB087206, AB198869, AB044091, AY123768 or AB234906). The DFR gene is particularly preferably a gene derived from *Gerbera* which is shown by accession number: Z17221 or a gene derived from *Torenia* which is shown by accession number: AB012924. Further, a novel gene which is found in the present invention such as the F3H gene (SEQ ID No: 50) which is derived from moth orchid, the DFR gene (SEQ ID No: 64) or the ANS gene (SEQ ID No: 74) may be used.

Further, the present invention relates to a recombinant vector containing such a gene, particularly an expression vector.

Depending on the host species into which the gene is introduced, the expression vector has an expression regulation region such as a promoter, a terminator, a DNA replication origin, etc. The promoter may, for example, be one which induces a gene expression in petal cells, and a promoter derived from a CHS (chalcone synthase) gene of moth orchid or a promoter derived from cauliflower mosaic virus (CaMV) 35S may be mentioned. Further, the terminator may, for example, be a terminator derived from a CHS gene of moth orchid or a terminator derived from cauliflower mosaic virus (CaMV) 35S.

Specifically, it is preferred that the F3'5'H gene of *Commelina communis* is connected to a 3' downstream of the promoter sequence, and a transcription termination sequence is added to a 3' downstream of the F3'5'H gene.

The F3H gene, the DFR gene and/or the ANS gene can also be connected to a 3' downstream of a promoter sequence and introduced into plants, like the F3'5'H gene.

The expression vector can be produced in accordance with a conventional method by using a restriction endonuclease, a ligase, etc. Further, transformation of hosts with the expression vector can also be carried out in accordance with a conventional method.

In the present invention, the method for expressing a gene in petal cells may, for example, be a microprojectile bombardment method, *Agrobacterium*-mediated transformation method, electroporation method, PEG method or virus-mediated transformation method.

Figure 7:
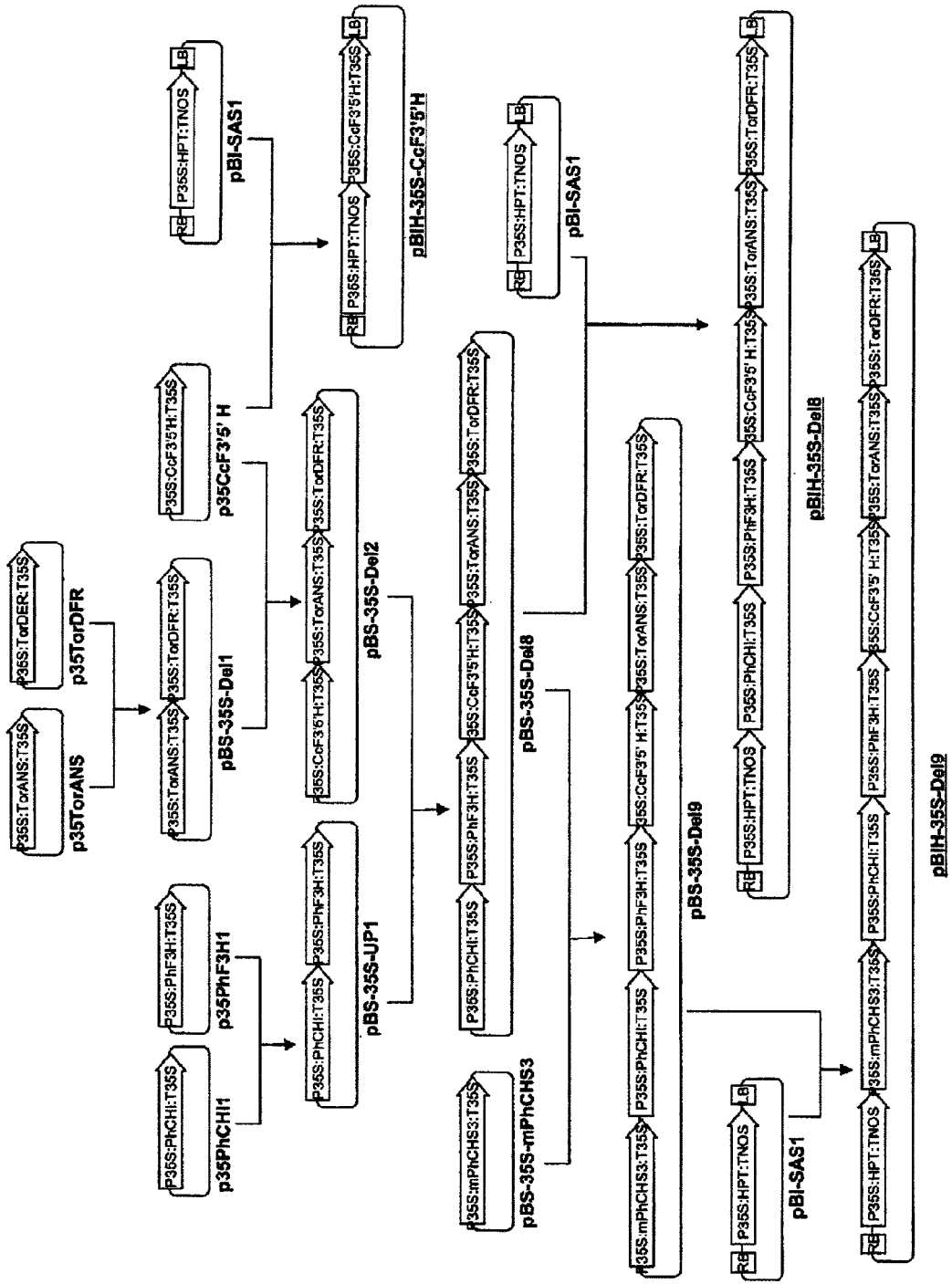
FIG. 7 is a schematic view (1) showing a procedure for construction of DNA for transformation of moth orchid.
Figure 8:
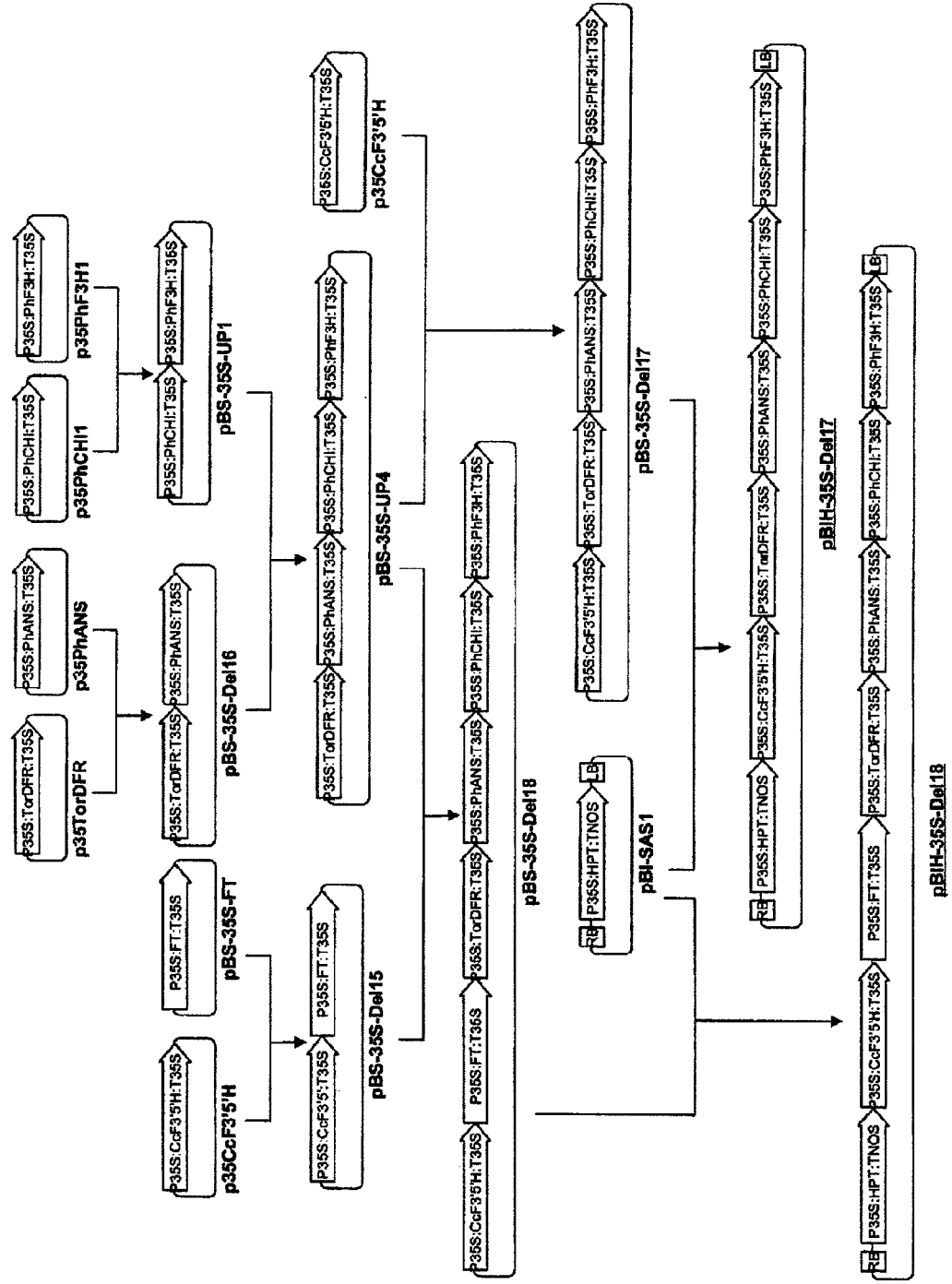
FIG. 8 is a schematic view (2) of a procedure for construction of DNA for transformation of moth orchid.

FIG. 7 (pBIH-35S-CcF3'5'H) shows one example of a vector for carrying out transformation with the F3'5'H gene by the *Agrobacterium*-mediated transformation method. Further, the F3H, DFR and ANS genes can also be constructed on the same vector as containing the *Commelina communis* F3'5'H gene independently or together (FIGS. 7 and 8).

In the present invention, plants to be transformed are flowering plants, preferably Orchids. The Orchids may, for example, be moth orchid, cymbidium, dendrobyobium, dendrochilum, oncidium, odontoglossum, mitonia or cattleya. Among them, moth orchid and cymbidium are preferred. *Cymbidium* is a plant which belongs to genus *Cymbidium*, and moth orchid includes genus *Phalaenopsis* and genus *Doritaenopsis*.

EXAMPLES

Now, the present invention will be described in further detail with reference to Examples. However these Examples are simply given to describe the present invention and as references of embodiments. These examples are to describe specific embodiments of the present invention and are not to restrict or limit the scope of the present invention. Further, it should be understood that various modes based on the technical concept of the present specification may be possible.

Further, general methods required for recombination of gene such as cutting and connecting DNA, transformation of *E. coli*, base sequence determination of a gene and PCR were basically carried out in accordance with manuals of commercially available reagents or apparatus used for each operation or experimental manual (such as "Molecular Cloning: A Laboratory Manual (Third Edition, Sambrook and Russell, 2001, Cold Spring Harbor Laboratory Press"). For PCR, GeneAmp PCR system 9700 (PE Applied Biosystems) was used. Unless otherwise specified, an apparatus was operated in accordance with a standard operation method described in a manual attached to the apparatus. Unless otherwise specified, all examples were carried out or may be carried out by using standard techniques, and such techniques are well known and common to those skills in the art.

As a homology searching program for examining an amino acid sequence encoded with the novel gene of the present invention and known amino acid sequences, BLASTP 2.2.15 (http://www.ddbj.nig.acjp/search/blast-j.html, Document: Altschul et al., Nucleic Acids Res. (1997) 25: 3389-3402) was used. Here, homology is the degree of similarity of amino acids over the entire sequence, and its value is obtained by aligning an amino acid sequence encoded with the novel gene and known amino acid sequences in order of the high similarity, and dividing the number of the homologous amino acids between them by the number of amino acids of the compared region. Here, high similarity is an alignment result output under a state (with gap, expected value 10, with filter) that the above BLASTP program parameter was defaulted. The homology described in the present Examples is one described with respect to a known amino acid sequence which showed the highest homology in the above homology analysis.

Example 1

Transfecting a Petal of Moth Orchid with a Gene

Unless otherwise specified in Examples of the present specification, a petal of moth orchid was transfected with each gene by the following gene transfection method, and its property was evaluated. All genes had a DNA structure having a promoter at 5' side and a terminator at 3' side and were introduced into a petal cell in the form so as to express in the cell.

A bud of moth orchid was sterilized with a 1 wt % of sodium hypochlorite aqueous solution for five minutes and washed with sterilized water 3 times. Then, the bud was resolved into a lateral sepal, dorsal sepal and petal, and the lateral sepal, dorsal sepal and petal were left on an agar medium containing New Dogashima Medium salt (Tokuhara and Mii, Plant Cell Reports (1993) 13: 7-11., hereinafter referred to as NDM salt) and 0.6 wt % of agarose. Here, in the case of *Phal. amabilis*, a bud having a length of about 15 mm was used, and in the case of Dtps. Queen Beer 'Mantenkou', a bud having a length of about 8 mm was used.

DNA to be introduced was purified by using Hi Speed Plasmid Midi Kit (QIAGEN), and the gene was introduced by the microprojectile bombardment method. Further, in a case where plural genes were introduced simultaneously, these DNA solutions were equally mixed one another, and such a mixture was used as a DNA solution for transfection.

At that time, the adsorption of DNA on gold particles was carried out at the following ratio. DNA dissolved in 20 µl of Tris/EDTA buffer (10 mM Tris-HCL, 1 mM EDTA, pH8.0) (Each 2 µg DNA of plasmid containing a gene was mixed and dissolved in the Tris/EDTA buffer.) was mixed with 50 µl of a gold particles suspension (the particle size: 1.0 µm, 60 mg/ml of 50% glycerol), and 50 µl of 2.5 M calcium chloride and 10 µl of 0.2 M spermidine were added to 70 µl of the mixture and suspended, whereby DNA was adsorbed on gold particles. Then, a supernatant was removed by centrifugal separation, and the particles were washed with 70% ethanol and 100% ethanol respectively. Then, 60 µl of 100% of ethanol was added to an obtained precipitate to prepare a suspension. The suspension was used as a sample solution, and 10 µl of the sample solution was used for one time of gene transfection. As a gene gun, IDERA GIE-III (TANAKA Co., Ltd.) was used. The gene transfection was carried out under a condition of the distance from a nozzle to a sample of 12 cm, under a reduced pressure of −80 kPa, a helium gas pressure of 0.3 MPa and spraying time of 0.025 second.

The petal after the gene transfection was left on an NDM salt agar medium and cultured under a light-dark cycle (light intensity: 23 µmol/m$^2$/s, light period: 16 hours, dark period: 8 hours) at 25° C.

Example 2

Searching and Cloning *Commelina communis* F3'5'H Gene (CcF3'5'H)

From a petal of a bud of the blue colored Asiatic dayflower (*Commelina communis*), all RNA was extracted by using RNeasy Plant Mini Kit (QIAGEN), and by using the RNA as a template, cDNA was prepared by using GeneRacer kit (Invitrogen).

Then, RT-PCR was carried out by using this cDNA as a template. Primers used for the PCR reaction were 35FH-1 (5'-ATGGTIGTIGARYTIATGAC-3'; SEQ ID No.: 3) and 35FH-4 (5'-CCRAAIGGIATIARYTCRAA-3'; SEQ ID NO.: 4) which were designed from a sequence of a conventionally known F3'5'H gene (GenBank accession No.: D14590, AJ011862, AB262585, D14589, AB078514, AY566988, D85184, AY275430, AF313490, AY675558, AB012925). In the reaction, a step of 98° C. for 10 seconds, 56° C. for 30 seconds and 72° C. for 1 minute was repeated 40 cycles. Further, Nested PCR was carried out by using an obtained reaction solution as a template and a primer 35FH-2 (5'-TGGATGGAYYTICARGGIAT-3'; SEQ ID NO.: 5) and a primer 35FH-3(5'-CCDATIGCCCADATRTTIAC-3'; SEQ ID NO.: 6). In the reaction, a step of 98° C. for 10 seconds, 56° C. for 30 seconds and 72° C. for 1 minute was repeated 40 cycles. An obtained reaction product was subjected to terminal blunting treatment and then cloning to HincII site of pUC18 (Takara Bio Inc.) to obtain p35FH23, and a partial DNA sequence contained in the p35FH23 was determined (CcF3'5'H partial sequence).

From the CcF3'5'H partial sequence, sequences of the 3' downstream side and 5' upstream side were analyzed by the RACE method.

The 3'RACE method was carried out by using a primer which can be designed from the CcF3'5'H partial sequence, the above *Commelina communis* RNA and GeneRacer kit (Invitrogen). The primers used in the PCR reaction were C35FH-3 (5'-ATCTCCCTCGTATCGCAACC-3'; SEQ ID NO.: 7) and GeneRacer 3' primer. In the reaction, a step of 98° C. for 10 seconds, 58° C. for 30 seconds and 72° C. for one minute was repeated 40 cycles. Nested PCR was carried out by using an obtained reaction solution as a template, a primer C35FH-4 (5'-GAAGCTTGTGAAGCCAATGG-3'; SEQ ID NO.: 8) and GeneRacer 3' Nested primer. In the reaction, a step of 98° C. for 10 seconds, 58° C. for 30 seconds and 72° C. for 1 minute was repeated 40 cycles. An obtained reaction product was subjected to termination blunting treatment and then cloning to HincII site of pUC18 (Takara Bio Inc.) to obtain p35FHC43', and a DNA sequence of a 3' downstream side contained in the p35FHC43' was determined (CcF3'5'H 3'RACE sequence).

The 5'RACE method was carried out by using a primer which can be designed from the CcF3'5'H partial sequence, the above *Commelina communis* RNA and GeneRacer kit (Invitrogen). The primers used in the PCR reaction were C35FH-6 (5'-CGTCGCCTCGTGCTCTCGCAGTATC-3'; SEQ ID NO.: 9) and GeneRacer 5' primer. In the reaction, a step of 98° C. for 10 seconds, 68° C. for 30 seconds and 72° C. for 1 minute was repeated 30 cycles. Nested PCR was carried out by using an obtained reaction solution as a template, a primer C35FH-5 (5'-TCTTCGAGAGCACCTTATC-GAACCTC-3'; SEQ ID NO.: 10) and GeneRacer 5' Nested primer. In the reaction, a step of 98° C. for 10 seconds, 68° C. for 30 seconds and 72° C. for 1 minute was repeated 30 cycles. An obtained reaction products was subjected to cloning to pCR4/TOPO10 (Invitrogen) to obtain p35FH5'5, and a DNA sequence of a 5' upstream side contained in the p35FH5'5 was determined (CcF3'5'H 5'RACE sequence).

The entire *Commelina communis* F3'5'H gene (CcF3'5'H) was subjected to cloning based on the CcF3'5'H 3'RACE sequence and the CcF3'5'H 5'RACE sequence. RT-PCR was carried out by using the above *Commelina communis* RNA as a template, a primer C35FH-7(5'-GAAAACCAATA-CAAAAACATACC-3'; SEQ ID NO.: 11), a primer C35FH-10 (5'-ATTGCTTCAAGTTCCCTAGC-3'; SEQ ID NO.: 12) and Ready-To-Go RT-PCR Beads (Amersham Biosciences). In the reaction, one step of 94° C. for 30 seconds, 54° C. for 30 seconds and 72° C. for 2 minutes was repeated 30 cycles. Further, semi Nested PCR was carried out by using an obtained reaction solution as a template, a primer C35FH-7 (SEQ ID NO.: 11) and C35FH-9 (5'-GTTCCCTAGCCCCG-TACCAC-3'; SEQ ID NO.: 13). In the reaction, a step of 98° C. for 10 seconds, 54° C. for 30 seconds and 72° C. for 1 minute was repeated 30 cycles. An obtained reaction product was subjected to cloning to pCR4/TOPO10 (Invitrogen) to obtain p35FH79. Then, a DNA sequence of the entire Asiatic dayflower F3'5'H gene contained in the p35FH79 was determined (CcF3'5'H; SEQ ID NO.: 1). Further, the sequence of the gene of the present invention found in *Commelina communis* is a novel gene. The amino acid sequence encoded by the base sequence has 61% homology to the amino acid sequence (GenBank accession No.: AY856345) encoded by the F3'5'H gene of delphinium by the homology analysis.

Example 3

Figure 2:
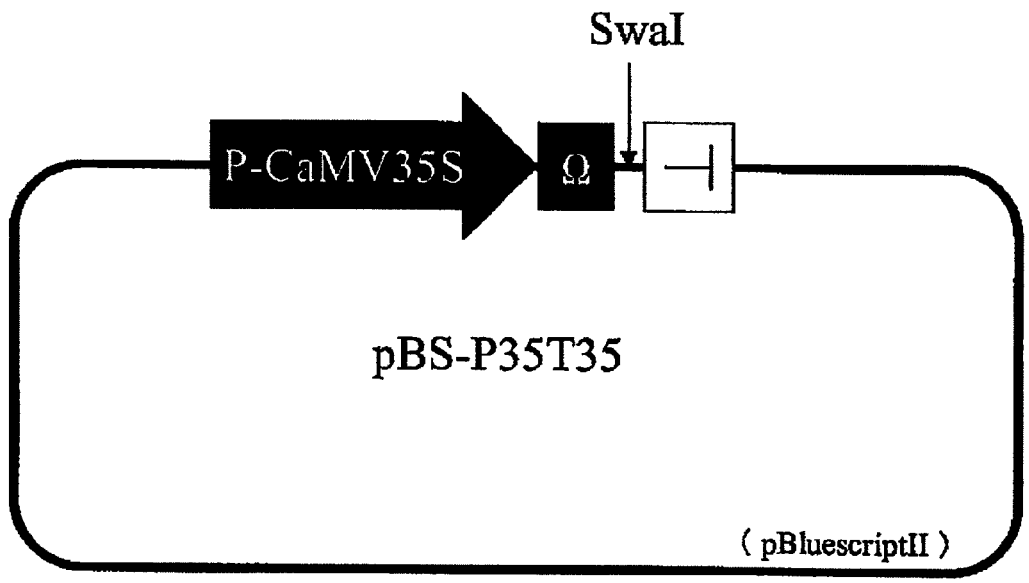
FIG. 2 is a plasmid vector used for transfecting a petal with a gene. P-CaMV35S is a cauliflower mosaic virus 35S promoter. Ω is an omega sequence of tobacco mosaic virus. T is a transcription termination sequence derived from a cauliflower mosaic virus.

Preparation of an Expression Vector (pBS-P35T35) for Gene Transfection pBS-P35T35 is a plasmid having a cauliflower mosaic virus 35S promoter (Hohn et al., Curent Topics in Microbiology and Immunology (1982) 96: 194-236), an omega sequence of tobacco mosaic virus (Gallie et al., Nucleic Acids Research (1987) 15: 3257-3273), a restriction endonuclease SwaI site and a cauliflower mosaic virus 35S terminator in this order in pBluescriptIISK-(Stratagene) (FIG. 2). A plasmid having the substantially same function as this pBS-P35T35 can be constructed as follows.

An oligonucleotide SAS-S (5'-CTAGCTAGCG-GCGCGCCTGCAGGATATCATTTAAATCCCGGG-3'; SEQ ID NO.: 14) and an oligonucleotide SAS-AS (5'-CCCGGGATTTAAATGATATCCTGCAG-GCGCGCCGCTAGCTAG-3'; SEQ ID NO.: 15) were denatured and then gradually cooled to room temperature. An obtained one was subjected to NheI treatment and connected to XbaI-EcoRV site of pBluescriptIISK-(Stratagene) to prepare pBS-SAS which is a plasmid DNA of which a restriction enzyme site is modified. A region amplified by PCR using a cauliflower mosaic virus genome DNA (GenBank accession V00140) as a template, a primer T-CaMV35S-SseI-F (5'-AACCTGCAGGAAATCACCAGTCTCTCTCTA-3'; SEQ ID NO.: 16) and a primer T-CaMV35S-AscI-R (5'-GGCGCGCCATCGATAAGGGGTTATTAG-3'; SEQ ID NO.: 17) was treated with a restriction endonuclease Sse8387I and AscI. This fragment was connected to Sse83871-AscI site of pBS-SAS to prepare pBS-T35S. Based on pJD301 (Leon et al., Plant Physiology (1991) 95: 968-972), a sequence of cauliflower mosaic virus 35S promoter which is cut by HindIII and HincII and an omega sequence of tobacco mosaic virus were connected to HindIII-SmaI site of pBS-T35S to prepare an expression vector (pBS-P35T35).

Example 4

Subcloning of the *Commelina communis* F3'5'H Gene to an Expression Vector

An Open Reading Frame part of the *Commelina communis* F3'5'H gene was amplified by PCR using a plasmid DNA (p35FH79) containing the above CcF3'5'H entire sequence as a template and was subjected to subcloning to an expression vector pBS-P35T35. The PCR was carried out by using a primer CcF35H-F (5'-ATGGTACCCCTTACGTACCTT-3'; SEQ ID NO.: 18), a primer CcF35H-R (5'-TTATGT-TGTTTTTATATTCTTATAAACG-3'; SEQ ID NO.: 19) and p35FH79 as a template. In the reaction, a step of 94° C. for 30 seconds, 52° C. for 30 seconds and 72° C. for 1 minute and 20 seconds was repeated 25 cycles. An obtained reaction product was subjected to cloning to SwaI site of pBS-P35T35 to obtain p35 CcF3'5'H. The p35 CcF3'5'H is DNA to express the *Commelina communis* F3'5'H gene in plant cells.

Example 5

Confirmation of Expression of the *Commelina communis* F3'5'H Gene

A petal of a red moth orchid (Dtps. Queen Beer 'Mantenkou') was transfected with 1.2 μg of the p35 CcF3'5'H by the method of Example 1 and cultured for 5 days, whereby many deep purple cells emerged at the petal. On the other hand, in a case where cells were transfected with gold particles containing no such a gene, the above phenomena was not observed.

Thus, it is considered that the isolated *Commelina communis* F3'5'H gene imparted a flavonoid 3'5'-hydroxylase activity to the petal cell of the moth orchid, and as a result, delphinidin which is a blue pigment was produced.

Example 6

Evaluation of Enzyme Activity of the *Commelina communis* F3'5'H Gene

The enzyme activity of the *Commelina communis* F3'5'H gene was evaluated by the amount of delphinidin which is a blue pigment and compared to an already known gene (Petunia gene) which is considered to be useful for producing blue carnation.

(1) Isolation of the Petunia F3'5'H Gene (PetF3'5'H)

All RNA was isolated from a petal of a bud of commercially available Petunia (hybrid) before blossom by using RNeasy Plant Mini Kit (QIAGEN). cDNA was prepared by using this RNA as a template and superscriptII First-Strand Synthesis System (Invitrogen). Then, RT-PCR was carried out by using this cDNA as a template. As primers for the PCR reaction, PetF3'5'H1-F (5'-ATGATGCTACTTACTGAGCT-TGGTG-3'; SEQ ID NO.: 20) and PetF3'5'H1-R (5'-CAA-CATGCGCAATTATAGCA-3'; SEQ ID NO.: 21) which were designed from two sequences (GenBank accession No.: A29011, A29013) of an already known petunia F3'5'H gene, or PetF3'5'H2-F(5'-ATGGTGCTACTTAGTGAGCTTGC-3'; SEQ ID NO.: 22) and PetF3'5'H2-R (5'-AACCAACG-TAAAGGCATGTT-3'; SEQ ID NO.: 23) were used. In both cases, the reaction was carried out by repeating a step of 94° C. for 30 seconds, 55° C. for 30 seconds and 72° C. for 2.5 minutes 45 cycles. Each obtained reaction product was subjected to cloning at SwaI site of pBS-P35T35 to obtain p35PetF3'5'H1 and p35PetF3'5'H2.

(2) Transfection with *Commelina communis* F3'S'H Gene and Petunia F3'5'H Gene

A petal of a red moth orchid (Dtps. Queen Beer 'Mantenkou') was transfected with 1.3 μg of either the p35 CcF3'5'H gene derived from *Commelina communis* or a gene (p35PetF3'5'H1 or p35PetF3'5'H2) derived from Petunia by the method of Example 1. Further, at the time of gene transfection, in order to measure efficiency of gene transfection, the petal was cotransfected with 0.17 μg of p35luc (Firefly Luciferase gene) as the internal standard. This p35luc was prepared by subcloning the blunt-ended Luciferase gene fragment, obtained by cutting pSP-luc+(Promega) with BglII-XbaI, into the blunt-ended pBI221 (CLONTECH) cut with BamHI and SacI.

The gene transfected petal was static cultured for 5 days, and then grinded in liquid nitrogen and suspended in 200 μl of 0.1×Passive Lysis Buffer (Dual-Luciferase Reporter Assay System, Promega) to prepare a sample. The Luciferase activity of the sample was measured, and the quantitative analysis of anthocyanidin was carried out.

Measurement of the Luciferase Activity

5 μl of 5×Passive Lysis Buffer (Promega) and 100 μl of Luciferase Assay Substrate (Promega) were added to 20 μl of the above sample, and then the Luciferase activity was measured by using luminometer flash'n glow LB955 (BERTHOLD TECHNOLOGIES) under a condition of measuring time of 10 seconds.

Quantitative Analysis of Delphinidin

400 μl of 2N hydrochloric acid was added to 150 μl of the above sample, and then hydrolysis treatment was carried out at 98° C. for 2 hours, and extraction with 200 μl of isoamylalcohol was carried out. The amount of delphinidin in the organic layer was measured by a liquid chromatography method under the following condition.

Apparatus: Waters2690 (Waters),
Column: Nucleosil 100-5C18 4.6×250 mm (GL. Sciences),
Column temperature: 40° C.,
Elution condition: Gradient (B liquid 20%→85% for 40 minutes, B liquid 85% for 5 minutes) was applied by using 1.5% of phosphoric acid solution (A liquid) and 1.5% phosphoric acid•20% acetic acid•25% acetonitrile aqueous solution (B liquid), and elution was carried out at a flow rate of 1 ml/minute.
Detection wavelength: 531 nm.

The amount of delphinidin was measured by an absolute analytical curve method using the standard (delphinidin hydrochloride). Further, the obtained amount of delphinidin was corrected by using Luciferase activity. Results are shown in Table 1. It is evident from Table 1 that the accumulated amount of delphinidin by the *Commelina communis* F3'5'H gene was higher by about five times than that of the Petunia F3'5'H2 gene. Further, the delphinidin was not detected from the sample using the Petunia F3'5'H1 gene.

TABLE 1

|   | CcF3'5'H | | | PetF3'5'H2 | | |
|---|---|---|---|---|---|---|
|   | Amount of delphinidin (pg/sample) | Luc assay (RLU/sample) | Pg/RLU | Amount of delphinidin (pg/sample) | Luc assay (RLU/sample) | Pg/RLU |
| 1 | 12400 | 265681 | 0.0467 | 4400 | 491562 | 0.0090 |
| 2 | 26200 | 743973 | 0.0352 | 13000 | 1063867 | 0.0122 |

TABLE 1-continued

| | CcF3'5'H | | | PetF3'5'H2 | | |
|---|---|---|---|---|---|---|
| | Amount of delphinidin (pg/sample) | Luc assay (RLU/sample) | Pg/RLU | Amount of delphinidin (pg/sample) | Luc assay (RLU/sample) | Pg/RLU |
| 3 | 50600 | 880990 | 0.0574 | 7400 | 757137 | 0.0098 |
| 4 | 37000 | 741444 | 0.0499 | 3200 | 530822 | 0.0060 |
| Average | | | 0.0473 | | | 0.0092 |
| SD | | | 0.0092 | | | 0.0026 |

Example 7

Transfection of a Petal of the White Moth Orchid with a F3'5'H Gene

In order to produce a blue moth orchid, a petal of white moth orchid (*Phal. amabilis*) was transfected with 1.6 μg of either a gene (p35 CcF3'5'H) derived from *Commelina communis* or a gene (p35PetF3'5'H1, p35PetF3'5'H2) derived from Petunia, like Example 6(2), in accordance with the method of Example 1. However, though the petal was transfected with such a gene, clear color change of the petal was not observed.

Therefore, a gene encoding the group of enzymes at the upstream of the F3'5'H in the anthocyanidin synthetic pathway (FIG. 1) ((1) Chalcone synthase: CHS, (2) Chalcone isomerase: CHI and (3) flavanone 3-hydroxylase: F3H) was isolated for transfection.

Example 8

Isolation of the Moth Orchid CHS Gene (PhCHS3)

All RNA was isolated from a petal just before blossom of moth orchid (Dtps. Sogo Vivien×Dtps. Sogo Yenlin) by using RNeasy Plant Mini Kit (QIAGEN). cDNA was prepared by using this RNA as a template and SuperscriptII First-Strand Synthesis System (Invitrogen). Then, RT-PCR was carried out by using this cDNA as a template. As primers for the PCR reaction, PhCHS3 F1 (5'-AAGCTTGTGAGAGAC-GACGGA-3'; SEQ ID NO.: 24) and PhCHS3 R1 (5'-TGGC-CCTAATCCTTCAAATT-3'; SEQ ID NO.: 25) which were designed from the known moth orchid CHS gene (PhCHS) sequence (GenBank accession No.: DQ089652) were used. The reaction was carried out by repeating a step of 94° C. for 30 seconds, 55° C. for 30 seconds and 72° C. for 1 minute 25 cycles. A reaction product was amplified by using this reaction solution as a template under the same condition again. An obtained reaction product was subjected to cloning at SwaI site of pBS-P35T35 to obtain p35PhCHS3. Then, a DNA sequence of the entire moth orchid CHS gene contained in p35PhCHS3 was determined (PhCHS3; SEQ ID NO.: 26). The p35PhCHS3 is DNA for expressing the moth orchid CHS gene in plant cells.

Example 9

Isolation of Moth Orchid CHI Gene (PhCHI1)

All RNA was isolated from a petal just before blossom of moth orchid (Dtps. Sogo Vivien×Dtps. Sogo Yenlin) by using RNeasy Plant Mini Kit (QIAGEN). cDNA was prepared by using this RNA as a template and SuperscriptII First-Strand Synthesis System (Invitrogen).

Then, RT-PCR was carried out by using this cDNA as a template. Various plants' CHI genes have been reported (GenBank accession No.: AY700850, AY086088, DQ160231, AJ004902, AF474923, XM_470129, U03433, AB187026). As primers for the PCR reaction, CHI-dgF1 (5'-TTYCTCGSYGGBGCMGGYGWVMGVGG-3'; SEQ ID NO.: 28) and CHI-dgR1 (5'-CMGGIGAIACVSCRTKY-TYICCRATVAT-3'; SEQ ID NO.: 29) which were designed from the conventionally known CHI gene were used. In the reaction, a step of 94° C. for 30 seconds and 72° C. for 1 minute was repeated 5 cycles, a step of 94° C. for 30 seconds and 70° C. for 1 minute was repeated 5 cycles, and then a step of 94° C. for 30 seconds, 68° C. for 30 seconds and 72° C. for 1 minute was repeated 25 cycles.

Further, Nested PCR was carried out by using an obtained reaction solution as a template, a primer CHI-dgF3(5'-TMIKYWCMGGISMITTYGARAARYT-3'; SEQ ID NO.: 30) and a primer CHI-dgR3 (5'-TYICCRATVATIGWHTC-CARIAYBGC-3'; SEQ ID NO.:31). In the reaction, a step of 94° C. for 30 seconds, 60° C. for 30 seconds and 72° C. for 1 minute was repeated 25 cycles. An obtained reaction product was subjected to cloning at pCR4-TOPO (Invitrogen) to obtain PhCHIfrag 16, and a partial DNA sequence contained in the PhCHIfrag 16 was determined (PhCHI partial sequence).

From the PhCHI partial sequence, sequences of the 3' downstream side and 5' upstream side were analyzed by the RACE method.

The 3'RACE method was carried out by using a primer which can be designed from the PhCHI partial sequence, the above RNA and GeneRacer kit (Invitrogen). The primers used in the PCR reaction were PhCHI-GSP F1 (5'-ATGCT-GCTGCCATTAACGGGTCA-3'; SEQ ID NO.: 32) and GeneRacer 3' primer. In the reaction, a step of 94° C. for 30 seconds and 72° C. for 1 minute was repeated 5 cycles, a step of 94° C. for 30 seconds and 70° C. for 1 minute was repeated 5 cycles, and then a step of 94° C. for 30 seconds, 60° C. for 30 seconds and 72° C. for 1 minute was repeated 25 cycles. Further, Nested PCR was carried out by using an obtained reaction solution as a template, a primer PhCHI-GSP F2 (5'-TCCGAGAAGGTCTCCGGGAACT-3'; SEQ ID NO.: 33) and GeneRacer 3' Nested primer. In the reaction, a step of 94° C. for 30 seconds, 60° C. for 30 seconds and 72° C. for 1 minute was repeated 25 cycles. An obtained reaction product was subjected to cloning to pCR4-TOPO (Invitrogen) to obtain PhCHI3'RACE23. A DNA sequence of the 3' downstream side contained in the PhCHI3'RACE23 were determined (PhCHI3'RACE sequence).

The 5'RACE method was carried out by using a primer which can be designed from the PhCHI partial sequence, the above RNA and GeneRacer kit (Invitrogen). The primers used in the PCR reaction were PhCHI-GSP R1 (5'-GCAT-TCGTCAGCTTCTTGCTCTCT-3'; SEQ ID NO.: 34) and GeneRacer 5' primer. In the reaction, a step of 94° C. for 30 seconds and 72° C. for 1 minute was repeated 5 cycles, a step of 94° C. for 30 seconds and 70° C. for 1 minute was repeated 5 cycles, and then a step of 94° C. for 30 seconds, 60° C. for 30 seconds and 72° C. for 1 minute was repeated 25 cycles. Further, Nested PCR was carried out by using an obtained reaction solution as a template, a primer PhCHI-GSP R2 (5'-ATCACATCAGTCTCAGCCACA-3'; SEQ ID NO.: 35) and GeneRacer 5' Nested primer. In the reaction, a step of 94° C. for 30 seconds, 60° C. for 30 seconds and 72° C. for 1 minute was repeated 25 cycles. An obtained reaction product was subjected to cloning to pCR4-TOPO (Invitrogen) to obtain PhCHI5'RACE54. A DNA sequences of the 5' upstream side contained in the PhCHI5'RACE54 was determined (PhCHI5'RACE sequence).

The entire of the moth orchid CHI gene (PhCHI) was subjected to cloning based on the PhCHI3'RACE sequence and the PhCHI5'RACE sequence. PCR was carried out by using the above cDNA, a primer PhCHI init (5'-ATGGCA-GAAACAGTGGCGACGCCCA-3'; SEQ ID NO.: 36) and a primer PhCHI term (5'-TCAAACGACTCCATCTTGCTC-3'; SEQ ID NO.: 37). In the reaction, a step of 94° C. for 30 seconds, 65° C. for 30 seconds and 72° C. for 1.5 minutes was repeated 45 cycles. An obtained reaction product was subjected to cloning to SwaI site of pBS-P35T35 to obtain p35PhCHI1. Then, a base sequence of the entire moth orchid CHI gene contained in the p35PhCHI1 was determined (Ph-CHI1, SEQ ID NO.: 38). Further, the present sequence of the gene found in moth orchid is a novel gene. The amino acid sequence encoded by the DNA sequence has 54% homology to the amino acid sequence (GenBank accession No.: DQ120521) encoded by the CHI gene of tea plant by the homology analysis. The p35PhCHI1 is DNA for expressing the moth orchid CHI gene in plant cells.

Example 10

Isolation of Moth Orchid F3H Gene (PhF3H1)

All RNA was isolated from a petal just before blossom of moth orchid (Dtps. Sogo Vivien×Dtps. Sogo Yenlin) by using RNeasy Plant Mini Kit (QIAGEN). cDNA was prepared by using this RNA as a template and SuperscriptII First-Strand Synthesis System (Invitrogen).

Then, RT-PCR was carried out by using this cDNA as a template. Various plants' F3H genes have been reported (GenBank accession No.: D0394303, AY221246, AJ493133, AY641730, AF184270, AB078956, AB078956, AB201760, AY669324, AF036093, AB211958, AB187027, AB234905). As primers for the PCR reaction, a primer F3H-dgF1 (5'-TIVGIGAYGARGABGARMGBCC1AA-3'; SEQ ID NO.: 40) and a primer F3H-dgR1 (5'-ACBGCYYGRTGRTCH-GCRTTCTTRAA-3'; SEQ ID NO.: 41) which were designed from the conventionally known F3H gene were used. In the reaction, a step of 94° C. for 30 seconds and 72° C. for 1 minute was repeated 5 cycles, a step of 94° C. for 30 seconds, and 70° C. for 1 minute was repeated 5 cycles, and then a step of 94° C. for 30 seconds, 68° C. for 30 seconds and 72° C. for 1 minute was repeated 25 cycles. Further, Nested PCR was carried out by using an obtained reaction solution as a template, a primer F3H-dgF3 (5'-AARYTBRGKTTYGAYATG-WCHGGIG-3'; SEQ ID NO.: 42) and a primer F3H-dgR3 (5'-GGHWSRACVGTDATCCAIGWBTT-3'; SEQ ID NO.: 43). In the reaction, a step of 94° C. for 30 seconds, 60° C. for 30 seconds and 72° C. for 1 minute was repeated 25 cycles. An obtained reaction product was subjected to cloning to pCR4-TOPO (Invitrogen) to obtain PhF3Hfrag 26, and a partial DNA sequence contained in the PhF3Hfrag 26 was determined (PhF3H partial sequence).

Sequences of the 3' downstream side and 5' upstream side from the PhF3H partial sequence were analyzed by the RACE method.

The 3'RACE method was carried out by using a primer which can be designed from the PhF3H partial sequence, the above RNA and GeneRacer kit (Invitrogen). The primers used in the PCR reaction were PhF3H-GSP F1 (5'-TTCT-CATACCCAATCGGGAG-3'; SEQ ID NO.: 44) and GeneRacer 3' primer. In the reaction, a step of 94° C. for 30 seconds and 72° C. for 1 minute was repeated 5 cycles, and a step of 94° C. for 30 seconds and 70° C. for 1 minute was repeated 5 cycles, and then a step of 94° C. for 30 seconds, 60° C. for 30 seconds and 72° C. for 1 minute was repeated 25 cycles. Further, Nested PCR was carried out by using an obtained reaction solution as a template, a primer PhF3H-GSP F2 (5'-AATCGGGAGCCGCGATTACT-3'; SEQ ID NO.: 45) and GeneRacer 3' Nested primer. In the reaction, a step of 94° C. for 30 seconds, 60° C. for 30 seconds and 72° C. for 1 minute was repeated 25 cycles. An obtained reaction product was subjected to cloning to pCR4-TOPO (Invitrogen) to obtain PhF3H3'RACE33. A DNA sequence of the 3' downstream side contained in the PhF3H3'RACE33 was determined (PhF3H 3'RACEsequence).

The 5'RACE method was carried out by using an oligonucleotide which can be designed from the PhF3H partial sequence, the above RNA and GeneRacer kit (Invitrogen). The primers used in the PCR reaction were PhF3H-GSPR1 (5'-TCTGTGTGGCGCTTCAGGCC-3'; SEQ ID NO.: 46) and GeneRacer 5' primer. In the reaction, a step of 94° C. for 30 seconds and 72° C. for 1 minute was repeated 5 cycles, and a step of 94° C. for 30 seconds and 70° C. for 1 minute was repeated 5 cycles, and then a step of 94° C. for 30 seconds, 60° C. for 30 seconds and 72° C. for 1 minute was repeated 25 cycles. Further, Nested PCR was carried out by using an obtained reaction solution, PhF3H-GSP R2 (5'-TGAGGTC-CGGTTGCGGGCATTTT-3'; SEQ ID NO.: 47) and GeneRacer 5' Nested primer. In the reaction, a step of 94° C. for 30 seconds, 60° C. for 30 seconds and 72° C. for 1 minute was repeated 25 cycles. An obtained reaction product was subjected to cloning to pCR4-TOPO (Invitrogen) to obtain PhF3H5'RACE86. A DNA sequence of the 5' upstream side contained in the PhF3H5'RACE86 was determined (PhF3H 5'RACEsequence).

The entire of the moth orchid F3H gene was subjected to cloning based on the PhF3H 3'RACE sequence and the PhF3H 5'RACE sequence. PCR was carried out by using the above cDNA, a primer PhF3H init. (5'-ATGGCCCCAATAC-CATTCCTACCGA-3'; SEQ ID NO.: 48) and a primer PhF3H term. (5'-CCTTAAGCTAAAATCTCATTTAATGC-CTTTGCTCC-3'; SEQ ID NO.: 49).

In the reaction, a step of 94° C. for 30 seconds, 65° C. for 30 seconds and 72° C. for 1.5 minute was repeated 40 cycles. An obtained reaction product was subjected to cloning to SwaI site of pBS-P35T35 to obtain p35PhF3H1. Then, a DNA sequence of the entire moth orchid F3H gene contained in the p35PhF3H1 was determined (PhF3H1; SEQ ID NO.: 50). Further, the sequence of the gene found in moth orchid is a novel gene. The amino acid sequence encoded by the DNA sequence has 86% homology to the amino acid sequence (GenBank accession No.: X89199) encoded by the F3H gene of *Bromheadia finlaysoniana*. The p35PhF3H1 is DNA for expressing the moth orchid F3H gene in plant cells.

Example 11

Transfection of a Petal of White Moth Orchid with the F3'5'H Gene and Anthocyanin Related Genes A petal of a white moth orchid (*Phal. amabilis*) was cotransfected with the CHS gene (p35PhCHS3: Example 8), CHI gene (p35PhCHI1: Example 9) and F3H gene (p35PhF3H1: Example 10) which were derived from moth orchid and the F3'5'H gene (p35 CcF3'5'H: Example 2) which was derived from *Commelina communis* in accordance with the method of Example 1. However, the color change of the petal was not observed.

Therefore, genes encoding enzymes ((1) dihydroflavonol 4-reductase: DFR and (2) anthocyanidin synthase: ANS) at downstream of the F3'5'H gene in the anthocyanin synthetic pathway were isolated for transfection.

Example 12

Isolation of Moth Orchid DFR Gene (PhDFR)

All RNA was isolated from a petal in a bud of moth orchid (Dtps. Queen Beer 'Mantenkou') by using RNeasy Plant Mini Kit (QIAGEN), and cDNA was prepared by using this RNA as a template and GeneRacer kit (Invitrogen).

Then, RT-PCR was carried out by using this cDNA as a template. Various plants' DFR genes have been reported (GenBank accession No.: AAB62873, AAC17843, AAD49343, AAQ83576, AAU93766, AAY32600, AAY32601, AAY32602, BAB40789, BAE79202). Primers used for the PCR reaction were DFRD-F1(5'-TTY-CAYGTIGCIACNCCNATG-3'; SEQ ID NO.: 52) and DFRD-R1(5'-DATNGCRTCRTCRAACATYTC-3'; SEQ ID NO.: 53) which were designed from the sequence of the above DFR gene. In the reaction, a step of 94° C. for 30 seconds, 48° C. for 30 seconds and 72° C. for 1 minute was repeated 40 cycles. Nested PCR was carried out by using an obtained reaction solution as a template, a primer DFRD-F2 (5'-AT-GAAYTTYCARWSIRARGAYCC-3'; SEQ ID NO.: 54) and a primer DFRD-R2 (5'-RCAIATRTAICKNCIRTTNGC-3'; SEQ ID NO.:55). In the reaction, a step of 94° C. for 30 seconds, 48° C. for 30 seconds and 72° C. for 1 minute was repeated 40 cycles. Further, Nested PCR was carried out again by using an obtained reaction solution as a template, a primer DFRD-F3 (5'-GARAAYGARGTNATHAARCC-3'; SEQ ID NO.: 56) and a primer DFRD-R3 (5'-RTCRTCIAR-RTGNACRAAYTG-3'; SEQ ID NO.:57). In the reaction, a step of 94° C. for 30 seconds, 48° C. for 30 seconds and 72° C. for 30 seconds was repeated 40 cycles. An obtained reaction product was subjected to cloning to pCR4/TOPO (Invitrogen) to obtain PhDFR-D/pCR4, and a partial DNA sequence contained in the PhDFR-D/pCR4 was determined (PhDFR partial sequence).

From the PhDFR partial sequence, sequences of the 3' downstream side and 5' upstream side were analyzed by the RACE method.

The 3'RACE method was carried out by using a primer which can be designed from the PhDFR partial sequence, the above RNA and GeneRacer kit (Invitrogen). The primers used for the PCR reaction were PhDFR-F1 (5'-GGTCATG-CAAAAGGTCGGGCAGCGTAA-3'; SEQ ID NO.: 58) and GeneRacer 3' primer. In the reaction, a step of 94° C. for 30 seconds and 72° C. for 1 minute was repeated 5 cycles, a step of 94° C. for 30 seconds and 70° C. for 1 minute was repeated 5 cycles, and then a step of 94° C. for 30 seconds, 68° C. for 30 seconds and 72° C. for 1 minute was repeated 25 cycles.

Further, Nested PCR was carried out by using an obtained reaction solution as a template, a primer PhDFR-F2 (5'-GT-GATCTTCACATCTTCCGCAGGAACAGT-3'; SEQ ID NO.: 59) and GeneRacer 3' Nested primer. In the reaction, a step of 94° C. for 30 seconds, 65° C. for 30 seconds and 72° C. for 1 minute was repeated 25 cycles. An obtained reaction product was subjected to cloning to pCR4/TOPO10 (Invitrogen) to obtain PhDFR3'RACE/pCR4, and a DNA sequence of 3' downstream side contained in the PhDFR3'RACE/pCR4 was determined (PhDFR3'RACE sequence).

The 5'RACE method was carried out by using a primer which can be designed from the PhDFR partial sequence, the above RNA and GeneRacer kit (Invitrogen). The primers used in the PCR reaction were PhDFR-R4 (5'-ATGATTCAT-TAAAAATCCGAAAAAAAGACCACTACAA-3'; SEQ ID NO.: 60) and GeneRacer 5' primer. In the reaction, a step of 94° C. for 30 seconds and 72° C. for 1 minute was repeated 5 cycles, a step of 94° C. for 30 seconds and 70° C. for 1 minute was repeated 5 cycles, and then a step of 94° C. for 30 seconds, 68° C. for 30 seconds and 72° C. for 1 minute was repeated 25 cycles. Further, Nested PCR was carried out by using an obtained reaction solution as a template, a primer PhDFR-R3 (5'-AACCATGCATAATAAAGCAGATGTG-TAAAT-3'; SEQ ID NO.: 61) and GeneRacer 5' Nested primer. In the reaction, a step of 94° C. for 30 seconds, 65° C. for 30 seconds and 72° C. for 1 minute was repeated 25 cycles. An obtained reaction product was subjected to cloning to pCR4/TOPO10 (Invitrogen) to obtain PhDFR 5'RACE/pCR4, and an upstream side DNA sequence contained in the PhDFR 5'RACE/pCR4 was determined (PhDFR 5'RACE sequence).

The entire moth orchid DFR gene was subjected to cloning based on the PhDFR3'RACE sequence and the PhDFR 5'RACE sequence. RT-PCR was carried out by using the above RNA, a primer PhDFR-F8A5 (5'-AAAAAATGGAG-GATGTGAGGAAGGGTCCTGTT-3'; SEQ ID NO.: 62), a primer PhDFR-R5 (5'-ACATGATTCATTAAAAATC-CGAAAAAAAGACCA-3'; SEQ ID NO.: 63) and Ready-To-Go You Prime First Strand Beads (Amersham Biosciences). In the reaction, a step of 98° C. for 30 seconds, 68° C. for 30 seconds and 72° C. for 1.5 minutes was repeated 35 cycles. An obtained reaction product was subjected to cloning to pBS-P35T35 to obtain p35PhDFR. Then, the entire DNA sequence of the DFR gene contained in the p35PhDFR was determined (PhDFR; SEQ ID NO.: 64). Further, the sequence of the gene found in moth orchid is a novel gene. The amino acid sequence encoded by the DNA sequence has 86% homology to the amino acid sequence (GenBank accession No.: AF007096) encoded by the DFR gene of *Bromheadia finlaysoniana* by the homology analysis. The p35PhDFR is DNA for expressing the moth orchid DFR gene in plant cells.

Example 13

Isolation of Moth Orchid ANS Gene (PhANS1)

All RNA was isolated from a petal in a bud just before blossom of moth orchid (Dtps. Queen Beer 'Mantenkou') by using RNeasy Plant Mini Kit (QIAGEN), and cDNA was prepared by using this RNA as a template and SuperscriptII First-Strand Synthesis System (Invitrogen).

Then, RT-PCR was carried out by using this cDNA as a template. Primers used for the PCR reaction were ANS-dgF2 (5'-TICARGGBTAYGGIAGYARRYTIGCIRMYA-3'; SEQ ID NO.: 66) and ANS-dgR2 (5'-GGYTCRCARAAIAYIRC-CCAIGADA-3'; SEQ ID NO.: 67) which were designed from a known ANS gene. In the reaction, a step of 94° C. for 30 seconds, 60° C. for 30 seconds and 72° C. for 1.5 minutes was repeated 40 cycles. By using an obtained reaction solution as a template and the same primers again, a step of 94° C. for 30 seconds, 56° C. for 30 seconds and 72° C. for 1 minute was repeated 30 cycles. An obtained reaction product was subjected to cloning to pCR4/TOPO10 (Invitrogen) to obtain PhANSfrag10, and a partial DNA sequence contained in the PhANSfrag10 was determined (PhANS partial sequence). From the PhANS partial sequence, sequences of the 3' downstream side and 5' upstream side were analyzed by the RACE method.

The 3'RACE method was carried out by using a primer which can be designed from the PhANS partial sequence, the above RNA and GeneRacer kit (Invitrogen). The primers used for the PCR reaction were PhANS3RACEGSP1 (5'-GCCCACACCGACGTCAGCTCCCTCTCCT-3'; SEQ ID NO.: 68) and GeneRacer 3' primer. In the reaction, a step of 94° C. for 30 seconds and 72° C. for 1.5 minutes was repeated 5 cycles, a step of 94° C. for 30 seconds and 70° C. for 1.5 minutes was repeated 5 cycles, and then a step of 94° C. for 30 seconds, 70° C. for 30 seconds and 72° C. for 1.5 minutes was repeated 25 cycles. Further, Nested PCR was carried out by using an obtained reaction solution as a template, a primer PhANS3RACEGSP2 (5'-CGTCGGGGATGCGCTC-GAGATCCTCAGC-3'; SEQ ID NO.: 69) and GeneRacer 3' Nested primer. In the reaction, a step of 94° C. for 10 seconds, 58° C. for 10 seconds and 72° C. for 1 minute was repeated 35 cycles. An obtained reaction product was subjected to cloning to pCR4/TOPO (Invitrogen) to obtain PhANS3'RACE37, and a DNA sequence of 3' down stream side contained in the PhANS3'RACE37 was determined (PhANS3'RACE sequence).

The 5'RACE method was carried out by using a primer which can be designed from the PhANS partial sequence, the above RNA and GeneRacer kit (Invitrogen). The primers used in the PCR reaction were PhANS5RACEGSP1 (5'-AGTCCGCGGGTTCAGTCGGCCAGATGGT-3'; SEQ ID NO.: 70) and GeneRacer 5' primer. In the reaction, a step of 94° C. for 30 seconds and 72° C. for 1.5 minutes was repeated 5 cycles, a step of 94° C. for 30 seconds and 70° C. for 1.5 minute was repeated 5 cycles, and then a step of 94° C. for 30 seconds, 70° C. for 30 seconds and 72° C. for 1.5 minutes was repeated 25 cycles. Nested PCR was carried out by using an obtained reaction solution as a template, a primer PhANS5RACEGSP2 (5'-CCGTCTTCTCCGGCGGGTA-GACGAGGTG-3'; SEQ ID NO.: 71) and GeneRacer 5' Nested primer. In the reaction, a step of 94° C. for 10 seconds, 58° C. for 10 seconds and 72° C. for 1 minute was repeated 35 cycles. An obtained reaction product was subjected to cloning to pCR4/TOPO (Invitrogen) to obtain PhANS5'RACE15, and an upstream side DNA sequence contained in the PhANS5'RACE15 was determined (PhANS 5'RACE sequence).

The entire moth orchid ANS gene was subjected to cloning based on the PhANS 3'RACE sequence and the PhANS 5'RACE sequence. PCR was carried out by using the above cDNA, a primer PhANS init (5'-ATGGCCACCAAAG-CAATCCCACC-3'; SEQ ID NO.: 72), and a primer PhANS term (5'-TCAATCCACAGGCGCCTTCT-3'; SEQ ID NO.: 73). In the reaction, a step of 94° C. for 30 seconds, 69° C. for 30 seconds and 72° C. for 1.5 minutes was repeated 35 cycles. An obtained reaction product was subjected to cloning to SwaI site of pBS-P35T35 to obtain p35PhANS1. Then, the entire base sequence of the ANS gene (PhANS1) contained in the p35PhANS1 was determined (PhANS1; SEQ ID NO.: 74). Further, the sequence of the present gene found in moth orchid is a novel gene. The amino acid sequence encoded by the DNA sequence has 58% homology to the amino acid sequence (GenBank accession No.: EF079869) encoded by the ANS gene of Anthurium by the homology analysis. The p35PhANS1 is DNA for expressing the moth orchid ANS gene in plant cells.

Example 14

Transfection of a Petal of White Moth Orchid with the F3'5'H Gene and an Anthocyanidin Related Gene A petal of a white moth orchid (*Phal. amabilis*) was cotransfected with the F3'5'H gene which was derived from *Commelina communis* and the CHS (p35PhCHS3), CHI (35PhCHI), F3H (p35PhF3H1), DFR (PhDFR) and AnS (PhANS1) genes which were derived from moth orchid in accordance with the method of Example 1. As a result, light blue cells were observed at the petal.

Therefore, it is evident that in order to change flower color of a white moth orchid to blue, the DFR gene and ANS gene are important. Thus, in order to change flower color to deeper blue, other plants' DFR genes and ANS genes were studied.

Example 15

Isolation and the DFR Gene and ANS Gene *Gerbera* and Cotransfection Therewith (1) Isolation of the *Gerbera* DFR Gene (GerDFR)
All RNA was isolated from a petal of a bud of commercially available *Gerbera* (hybrid) by using RNeasy Plant Mini Kit (QIAGEN), and cDNA was prepared by using this RNA as a template and SuperscriptII First-Strand Synthesis System (Invitrogen). Then, RT-PCR was carried out by using this cDNA as a template. As primers for the PCR reaction, GerDFR-F (5'-ATGGAAGAGGATTCTCCGGC-3'; SEQ ID NO.: 76) and GerDFR-R (5'-CTATTGGCCTTCTTTTGAA-CAACAAA-3'; SEQ ID NO.: 77) which were designed from a sequence (GenBank accession No.: Z17221) of a known *Gerbera* DFR gene (GerDFR) were used. The reaction was carried out by repeating a step of 98° C. for 10 seconds, 55° C. for 10 seconds and 72° C. for 1 minute and 30 seconds 45 cycles. An obtained reaction product was subjected to cloning to SwaI site of pBS-P35T35 to obtain a *Gerbera* DFR gene (p35GerDFR). The p35GerDFR is DNA for expressing the *Gerbera* DFR gene in plant cells.
(2) Isolation of *Gerbera* ANS Gene (GerANS)
RT-PCR was carried out by using the above cDNA as a template. Primers used for the PCR reaction were GerANS-F (5'-ATGGTGATTCAAGCAACCACA-3'; SEQ ID NO.: 78) and GerANS-R (5'-CTAGTTTTGCATCACTTCGTCTT-TAT-3'; SEQ ID NO.: 79) which were designed from a sequence (GenBank accession No.: AY997842) of a known *Gerbera* ANS gene (GerANS).

In the reaction, a step of 94° C. for 30 seconds, 56° C. for 30 seconds and 72° C. for 1 minute and 10 seconds was repeated 45 cycles. An obtained reaction product was subjected to cloning to SwaI site of pBS-P35T35 to obtain *Gerbera* ANS gene (p35GerANS). The p35GerANS is DNA for expressing the *Gerbera* ANS gene in plant cells.
(3) Cotransfection with the *Gerbera* DFR Gene and the Ger-ANS Gene A petal of a white moth orchid (*Phal. amabilis*) was cotransfected with the respective genes of the CHS (PhCHS3), CHI (PhCHI1) and F3H (PhF3H1) which were derived from moth orchid, the F3'5'H gene (CcF3'5'H) which was derived from *Commelina communis* and the DFR gene (GerDFR) and ANS gene (GerANS) which were derived from *Gerbera*. As a result, deeper blue-purple newly emerged at the petal, as compared to Example 14.

Example 16

Isolation of *Torenia* DFR Gene and ANS Gene and Cotransfection Therewith (1) Isolation of *Torenia* DFR Gene (TorDFR)

All RNA was isolated from a petal in a bud of a conventionally available *Torenia* (*Torenia fournieri*) by using RNeasy Plant Mini Kit (QIAGEN), and cDNA was prepared by using SuperscriptII First-Strand Synthesis System (Invitrogen). RT-PCR was carried out by using this cDNA as a template. Primers used for the PCR reaction were an oligonucleotide TorDFR-F (5'-ATGAGCATGGAAGTAGTAGTACCA-3'; SEQ ID NO.: 80) and TorDFR-R (5'-CTATTCTATCTTATGTTCTC-CATGG-3'; SEQ ID NO.: 81) which were designed from a sequence (GenBank accession AB012924) of an already known *Torenia* DFR gene (TorDFR). In the reaction, a step of 94° C. for 30 seconds, 56° C. for 30 seconds and 72° C. for 1 minute and 10 seconds was repeated 45 cycles. An obtained reaction product was subjected to cloning to SwaI site of pBS-P35T35 to obtain a *Torenia* DFR gene (p35TorDFR). The p35TorDFR is DNA for expressing the *Torenia* DFR gene in plant cells.

(2) Isolation of *Torenia* ANS Gene (TorANS)

RT-PCR was carried out by using the above cDNA as a template. Primers used for the PCR reaction were TorANS-F (5'-ATGGTTTCTCCAGCATCTCCGA-3'; SEQ ID NO.: 82) and TorANS-R (5'-TCACTCAACACTCTTATCATCAT-GCTC-3'; SEQ ID NO.: 83) which were designed from a sequence (GenBank accession AB044091) of a known *Torenia* ANS gene (TorANS). In the reaction, a step of 94° C. for 30 seconds, 56° C. for 30 seconds and 72° C. for 1 minute and 10 seconds was repeated 45 cycles. An obtained reaction product was subjected to cloning to SwaI site of pBS-P35T35 to obtain a *Torenia* ANS gene (p35TorANS). The p35TorANS is DNA for expressing ANS gene in plant cells.

(3) Cotransfection of *Torenia* DFR Gene and *Torenia* ANS Gene

A petal of a white moth orchid (*Phal. amabilis*) was cotransfected with respective genes of CHS (PhCHS3), CHI (PhCHI1) and F3H (PhF3H1) which were derived from moth orchid, the F3'5'H gene (CcF3'5'H) which was derived from *Commelina communis* and the DFR gene (TorDFR) and ANS gene (TorANS) which were derived from *Torenia* in accordance with the method of Example 1, and as a result, cells having a deeper blue purple than that of Example 14 newly emerged at the petal.

Examination of the Best DFR Gene and ANS Gene

With respect to the changing white moth orchid to blue color, different genes derived from plants were introduced in order to find the best DFR gene and ANS gene, and such genes were compared and examined.

Example 17

Observation of Coloration of the Petal Cell

The coloration of the petal cells was observed by stereomicroscope SZX12 (OLYMPUS Corporation) and macroscopically observed. The standard of the degree of the coloration of the petal was that one which could be macroscopically observed was judged as "III", one which could be observed by a stereomicroscope with a magnification of at most 32 times was judged as "II", and one which could not be observed by a stereomicroscope with a magnification of at least 32 times was judged as "I", and one wherein coloration was not observed as judged as "-".

Example 18

Comparison of the ANS Genes in the Petal of the White Moth Orchid

A petal of a white moth orchid (*Phal. amabilis*) was transfected with one of the following three sets of genes wherein only an ANS gene varied, and the degree of coloration was observed.

(1) Moth orchid ANS gene (PhANS1)+Moth orchid CHS gene (PhCHS3)+Moth orchid CHI gene (PhCHI1)+Moth orchid F3H gene (PhF3H1)+*Commelina communis* F3'5'H gene (CcF3'5'H)+*Gerbera* DFR gene (GerDFR)

(2) *Gerbera* ANS gene (GerANS)+Moth orchid CHS gene (PhCHS3)+Moth orchid CHI gene (PhCHI1)+Moth orchid F3H gene (PhF3H1)+*Commelina communis* F3'5'H gene (CcF3'5'H)+*Gerbera* DFR gene (GerDFR)

(3) *Torenia* ANS gene (TorANS)+Moth orchid CHS gene (PhCHS3)+Moth orchid CHI gene (PhCHI1)+Moth orchid F3H gene (PhF3H1)+*Commelina communis* F3'5'H gene (CcF3'5'H)+*Gerbera* DFR gene (GerDFR)

Figure 3:
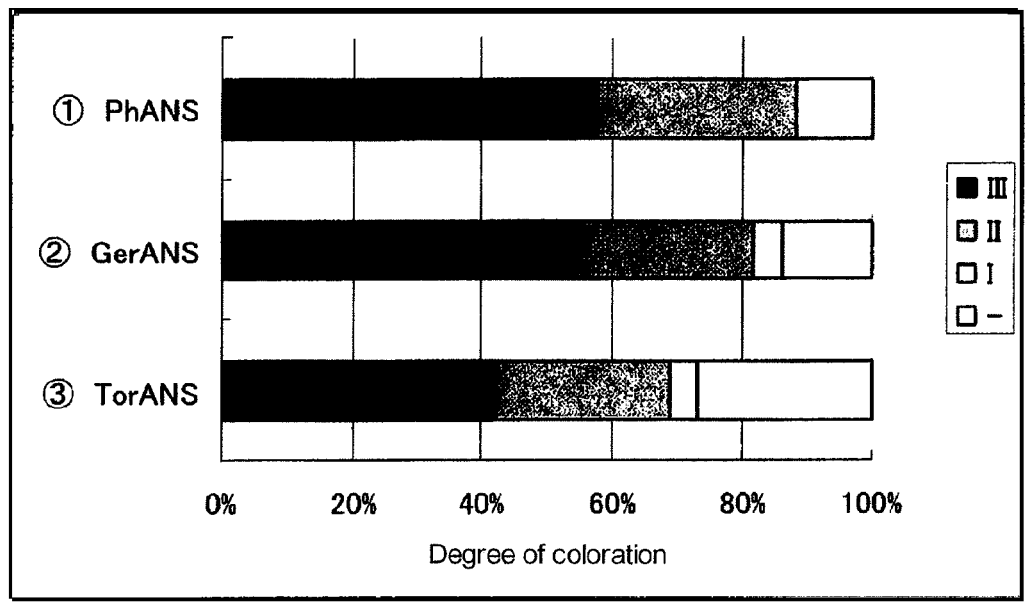
FIG. 3 is transfection of a petal of *Phal. amabilis* with a different ANS gene derived from a plant.

As a result, blue purple cells emerges on respective samples. The degrees of coloration of blue purple cells which emerged at twenty two pieces of the petal were compared. Results are shown on FIG. 3.

Example 19

Comparison of the DFR Genes in the Petal of the White Moth Orchid

A petal of a white moth orchid (*Phal. amabilis*) was transfected with one of the following three sets of genes wherein only a DFR gene varied, and the degree of coloration was observed.

(1) Moth orchid DFR gene (Ph DFR)+Moth orchid CHS gene (PhCHS3)+Moth orchid CHI gene (PhCHI1)+Moth orchid F3H gene (PhF3H1)+*Commelina communis* F3'5'H gene (CcF3'5'H)+Torenea ANS gene (TorANS)

(2) *Gerbera* DFR gene (Ger DFR)+Moth orchid CHS gene (PhCHS3)+Moth orchid CHI gene (PhCHI1)+Moth orchid F3H gene (PhF3H1)+*Commelina communis*F3'5'H gene (CcF3'5'H)+Torenea ANS gene (TorANS)

(3) *Torenia* DFR gene (TorDFR)+Moth orchid CHS gene (PhCHS3)+Moth orchid CHI gene (PhCHI1)+Moth orchid F3H gene (PhF3H1)+*Commelina communis* F3'5'H gene (CcF3'5'H)+Torenea ANS gene (TorANS)

Figure 4:
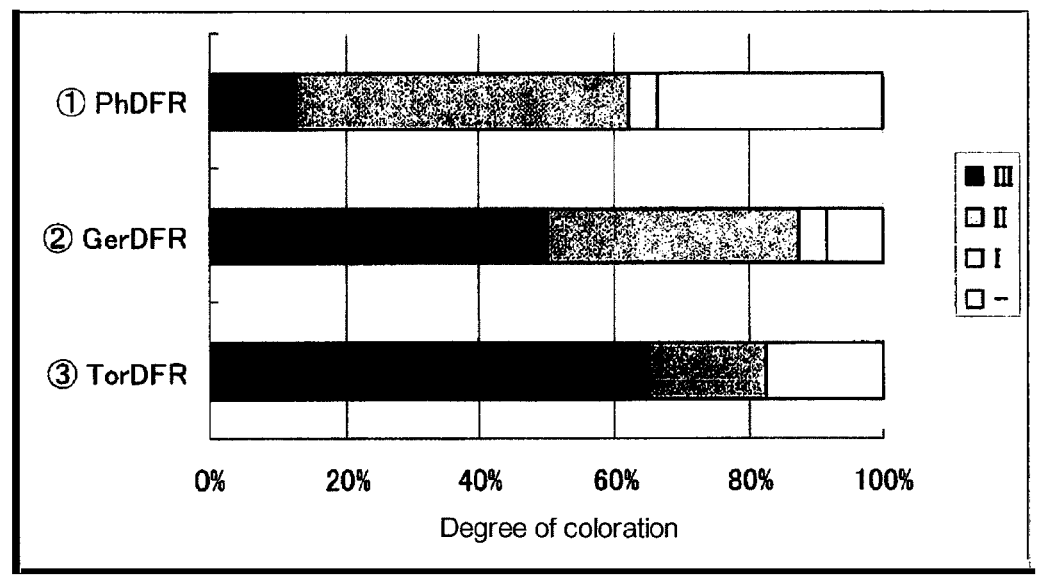
FIG. 4 is transfection of a petal of *Phal. amabilis* with a different DFR gene derived from a plant.

As a result, blue purple cells emerges on respective samples. The degree of coloration of blue purple cells which emerged at twenty three pieces of the petal was compared. Results are shown on FIG. 4. When the PhDFR gene was used, the degree of blue-purple coloration was low, as compared to the case where the GerDFR gene or the TorDFR gene was used. It is considered that in order to produce deep blue-purple flower color, the *Gerbera* DFR gene (Ger DFR) and the *Torenia* DFR gene (TorDFR) are superior to the endogenous moth orchid DFR gene (PhDFR).

Example 20

Performance of the *Commelina communis* F3'5'H Gene

In order to measure the performance of the *Commelina communis* F3'5'H gene on the white moth orchid, comparative tests with the petunia gene was carried out.

A petal of a white moth orchid (*Phal. amabilis*) was cotransfected with the *Commelina communis* F3'5'H gene ((1) CcF3'5'H) or a petunia F3'5'H gene ((2) PetF3'5'H1, or (3) PetF3'5'H2), together with the CHS gene (PhCHS3), CHI gene (PhCHI1) and F3H gene (PhF3H1) which were derived from moth orchid and the DFR gene (GerDFR) and ANS gene (GerANS) which were derived from *Gerbera*.

Figure 5:
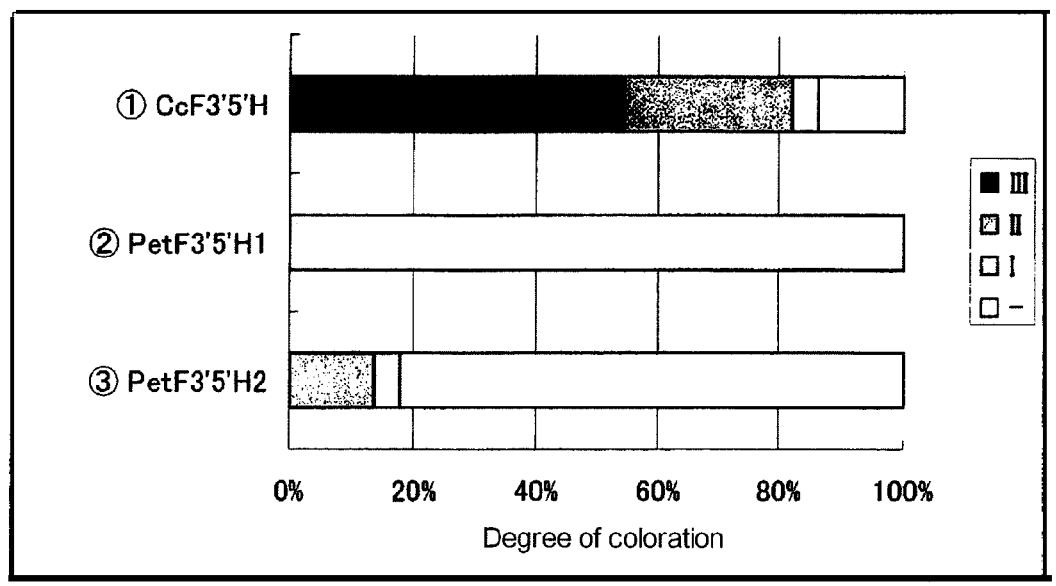
FIG. 5 is transfection of a petal of *Phal. amabilis* with a different F3'5'H gene derived from a plant.

As a result, in a case where the petunia F3'5'H gene (PetF3'5'H1) or the petunia F3'5'H2 gene (PetF3'5'H2) was used, blue coloration was little. On the other hand, in a case where the *Commelina communis* F3'5'H gene (CcF3'5'H) was used, clear coloration was observed (FIG. 5).

Example 21

Necessity of Gene Transfection with F3H, CHI, CHS Genes

Necessity of respective genes in the blue color change of white moth orchids was examined. A petal of a white moth orchid (*Phal. amabilis*) as a material was transfected with the following four types of gene sets, and the degree of coloration was observed.

(1) *Commelina communis* F3'5'H gene (CcF3'5'H)+*Torenia* DFR gene (TorDFR)+*Torenia* ANS gene (TorANS)

(2) Moth orchid F3H gene (PhF3H1)+*Commelina communis* F3'5'H gene (CcF3'5'H)+*Torenia* DFR gene (TorDFR)+*Torenia* ANS gene (TorANS)

(3) Moth orchid CHI gene (PhCHI1)+Moth orchid F3H gene (PhF3H1)+*Commelina communis* F3'5'H gene (CcF3'5'H)+*Torenia* DFR gene (TorDFR)+*Torenia* ANS gene (TorANS)

(4) Moth orchid CHS gene (PhCHS3)+Moth orchid CHI gene (PhCHI1)+Moth orchid F3H gene (PhF3H1)+*Commelina communis* F3'5'H gene (CcF3'5'H)+*Torenia* DFR gene (TorDFR)+*Torenia* ANS Gene (TorANS)

Figure 6:
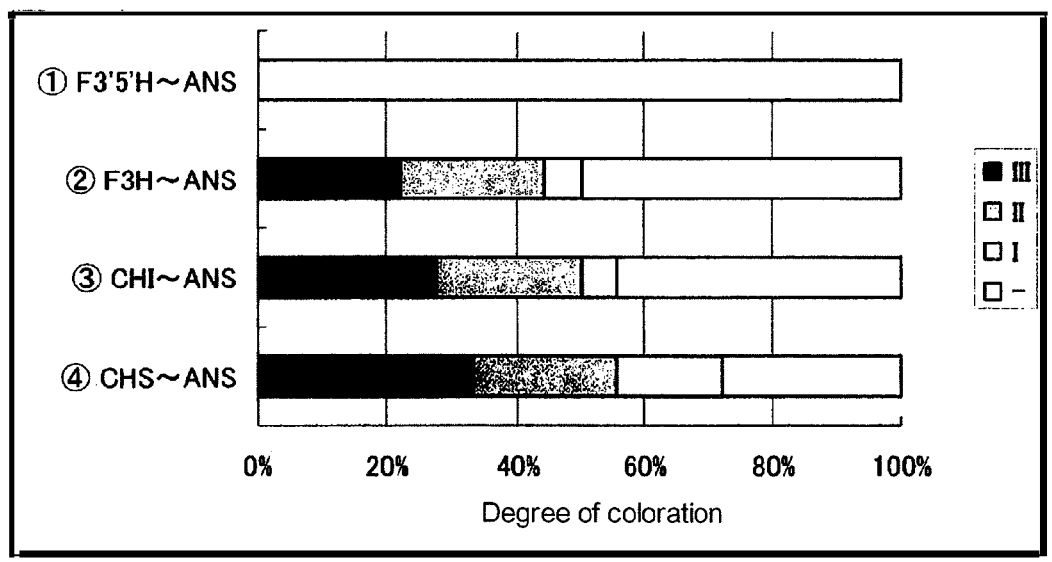
FIG. 6 is an identification of a gene required for changing the flower color of a white moth orchid.

A petal of *Phal. amabilis* was transfected with these genes, and the coloration of cells was observed. As a result, except (1), blue purple cells emerged. The degrees of coloration of 18 pieces of respective samples were compared, and results are shown in FIG. 6. From the results, it is evident that the F3H gene (PhF3H1) is essential for coloration.

Example 22

Analysis of Pigments Emerged by Transfecting a Petal of White Moth Orchids

In the above experiment, whether pigments contained in the blue purple cells which emerged at the petal of the white moth orchid (*Phal. amabilis*) was a delphinidin related pigment or not was examined. A petal of white moth orchid (*Phal. amabilis*) is cotransfected with the CHI gene, F3H gene and ANS gene which were derived from moth orchid, the DFR gene which was derived from *Gerbera* and the F3'5'H gene which was derived from *Commelina communis*, the petal was cultured for 0.5 days, and anthocyanidin was extracted from the petal in the same manner as in Example 6 and analyzed. As a result, delphinidin was detected as the main component of the pigment. The amount of the detected delphinidin was 16 ng per one sample (average of five samples). On the other hand, in the case of the group wherein the *Commelina communis* F3'5'H gene was excluded from the above gene sets, delphinidin was not detected. From the above result, it is evident that blue purple cells observed at the gene transfection of the white moth orchid were colored by a delphinidin derivative.

Example 23

Application to White Moth Orchid Other than *Phal. Amabilis*

A petal of a bud having a length of 1.7 cm of a pure white large moth orchid (Phal. White Star) was cotransfected with the CHS gene, CHI gene and F3H gene which were derived from moth orchid, the DFR gene and ANS gene which were derived from *Gerbera* and the F3'5'H gene which was derived from *Commelina communis* in accordance with the method of Example 1, and new blue purple cells emerged at the petal.

Example 24

Preparation of DNA for Moth Orchid Transformation by the *Agrobacterium* Method

Transformation of moth orchids can be carried out by the *Agrobacterium* method, as well as the microprojectile bombardment method (Belamino and Mii, Plant Cell Reports (2000) 19:435-442., Mishiba et al., Plant Cell Reports (2005) 24: 297-303). DNA for transformation to obtain gene recombinant plants by these methods was constructed. Maps and preparation procedures of respective plasmids are shown on FIGS. 7 and 8.

(1) Construction of pBI-SAS1

A short fragment obtained by cutting pBS-SAS of Example 04 with NotI and HindIII was subjected to subcloning to a part that pBI-RHL described on PCT/JP02/12268 was cut with NotI and HindIII to construct pBI-SAS1. The pBI-SAS1 is a plasmid which imparts hygromycin resistance to plants by transformation with *Agrobacterium*.

(2) pBS-35S-FT construction

Since a period of at least one year is required for blossom of moth orchids, DNA for expressing flowering gene FT (Kobayashi et al., Science (1999) 286: 1960-1962.) in moth orchids was constructed.

FTcDNA was prepared by amplifying all RNA prepared from whole plant of *Arabidopsis* by RT-PCR. For the PCR, AtFT 2nd-F (5'-GAAACCACCTGTTTGTTCAAGA-3'; SEQ ID NO.: 84) and AtFT 2nd-R (5'-TCAATTGGT-TATAAAGGAAGAAGC-3'; SEQ: 85) were used as primer, a purified FT cDNA was inserted to a part formed by cutting pBS-P35T35 with SwaI, clone into which cDNA was inserted to a sense direction was selected to construct pBS-P35S-FT. The pBS-35S-FT is a plasmid of which transcription is controlled by CaMV 35S promoter and CaMV 35S terminator.

(3) Construction of pBIH-35S-CcF3'5'H

The p35 CcF3'5'H was cut with BamHI, and a cohesive end was blunted with a Klenow fragment, followed by cutting with AscI to cut out a DNA fragment from the plasmid. This DNA fragment was inserted to a part formed by cutting pBI-SAS1 with AscI and SwaI to construct pBIH-35S-CcF3'5'H. The pBIH-35S-CcF3'5'H is a binary vector having a T-DNA region wherein HPT which is a selection marker and CcF3'5'H of which transcription is controlled by CaMV 35S promoter and CaMV 35S terminator are connected in this order.

(4) pBS-35S-mPhCHS3 Construction

A nucleotide substitution without an amino acid substitution was introduced into a SphI cut part in the PhCHS3 cDNA to prepare a cDNA which could not be cut with SphI. PhCHS3-1038F (5'-GTAACATGTCGAGCGCTTGCGT-TCTTTTCATACTCG-3'; SEQ ID NO.: 86) and PhCHS3-1073R (5'-CGAGTATGAAAAGAACGCAAGCGCTCGA-CATGTTAC-3'; SEQ ID NO.: 87) were used as primers for the nucleotide substitution, and cDNA was synthesized by using the pBS-35S-PhCHS3 as a template and Pyrobest (Takara Bio Inc.). Then, the template plasmid was digested by DpnI treatment to construct pBS-35S-mPhCHS3.

(5) Construction of pBS-35S-UP1

After cutting p35PhCHI1 with AscI, and a cohesive end was blunted with Klenow fragment, followed by cutting with SphI to cut out a DNA fragment from the plasmid. This DNA fragment was inserted into a part formed by cutting p35PhF3H1 with XbaI, blunting a cohesive end with a Klenow fragment, followed by cutting with SphI to construct pBS-35S-UP1. The pBS-35S-UP1 is a plasmid wherein respective cDNA of which transcription is controlled by CaMV 35S promoter and CaMV 35S terminator are connected in the order of PhCHI1 and PhF3H1.

(6) Construction of pBS-35S-Del1

The p35TorANS was cut with AscI, and a cohesive end was blunted with a Klenow fragment, followed by cutting with KpnI to cut out a DNA fragment from the plasmid. This DNA fragment was inserted into a part formed by cutting p35TorDFR with XbaI, and blunting a cohesive end with a Klenow fragment, followed by cutting with KpnI to construct pBS-35S-Del1. The pBS-35S-Del1 is a plasmid wherein respective cDNA of which transcription is controlled by CaMV 35S promoter and CaMV 35S terminator are connected in the order of TorANS and TorDFR.

(7) Construction of pBS-35S-Del2

The p35 CcF3'5'H was cut with AscI, a cohesive end was blunted with a Klenow fragment, and a DNA fragment was cutout by cutting the plasmid with SphI. This DNA fragment was inserted into a part formed by cutting the pBS-35S-Del1 with XbaI, and blunting a cohesive end with a Klenow fragment, followed by cutting with SphI to construct pBS-35S-Del2. The pBS-35S-Del2 is a plasmid in which respective cDNA of which transcription is controlled by CaMV 35S promoter and CaMV 35S terminator in the order of CcF3'5'H, TorANS and TorDFR.

(8) Construction of pBS-35S-Del8

The pBS-35S-UP1 was cut with AscI, and a cohesive end was blunted with a Klenow fragment, followed by cutting with SphI to cut out a DNA fragment from the plasmid. This DNA fragment was inserted into a part formed by cutting the pBS-35S-Del2 with XbaI, and blunting a cohesive end with a Klenow fragment, followed by cutting with SphI to construct pBS-35S-Del8. The pBS-35S-Del8 is a plasmid wherein respective cDNA of which transcription is controlled by CaMV 35S promoter and CaMV 35S terminator are connected in the order of PhCHI1, PhF3H1, CcF3'5'H, TorANS and TorDFR.

(9) Construction of pBS-35S-Del9

The pBS-35S-mPhCHS3 was cut with AscI, and a cohesive end was blunted with a Klenow fragment, followed by cutting with SphI to cut out a DNA fragment from the plasmid. This DNA fragment was inserted into a part formed by cutting the pBS-35S-Del8 with XbaI, and blunting a cohesive end with a Klenow fragment, followed by cutting with SphI to construct pBS-35S-Del9. The pBS-35S-Del9 is a plasmid wherein respective cDNA of which transcription is controlled by CaMV 35S promoter and CaMV 35S terminator are connected in the order of mPhCHS3, PhCHI1, PhF3H1, CcF3'5'H, TorANS and TorDFR.

(10) Construction of pBS-35S-Del15

The p35 CcF3'5'H was cut with AscI, and a cohesive end was blunted with a Klenow fragment, followed by cutting with SphI to cut out a DNA fragment from the plasmid. This DNA fragment was inserted into a part formed by cutting the pBS-35S-FT with XbaI, and blunting a cohesive end with a Klenow fragment, followed by cutting with SphI to construct pBS-35S-Del15. The pBS-35S-Del15 is a plasmid wherein respective cDNA of which transcription is controlled by CaMV 35S promoter and CaMV 35S terminator are connected in the order of CcF3'5'H and FT.

(11) Construction of pBS-35S-Del16

The p35 TorDFR was cut with AscI, and a cohesive end was blunted with a Klenow fragment, followed by cutting with SphI to cut out a DNA fragment from the plasmid. This DNA fragment was inserted into a part formed by cutting p35-PhANS1 with XbaI, and blunting a cohesive end with a Klenow fragment, followed by cutting with SphI to construct pBS-35S-Del16. The pBS-35S-Del16 is a plasmid wherein respective cDNA of which transcription is controlled by CaMV 35S promoter and CaMV 35S terminator are connected in the order of TorDFR and PhANS1.

(12) Construction of pBS-35S-UP4

The pBS-35S-Del16 was cut with AscI, and a cohesive end was blunted with a Klenow fragment, followed by cutting with SphI to cut out a DNA fragment from the plasmid. This DNA fragment was inserted into a part formed by cutting the pBS-35S-UP1 with XbaI, and blunting a cohesive end with a Klenow fragment, followed by cutting with SphI to construct pBS-35S-UP4. The pBS-35S-UP4 is a plasmid wherein respective cDNA of which transcription is controlled by CaMV 35S promoter and CaMV 35S terminator are connected in the order of TorDFR, PhANS1, PhCHI1 and PhF3H1.

(13) Construction of pBS-35S-Del17

The p35 CcF3'5'H was cut with AscI, and a cohesive end was blunted with a Klenow fragment, followed by cutting with SphI to cut out a DNA fragment from the plasmid. This DNA fragment was inserted into a part formed by cutting the pBS-35S-UP4 with XbaI, and blunting a cohesive end with a Klenow fragment, followed by cutting with SphI to construct pBS-35S-Del17. The pBS-35S-Del17 is a plasmid wherein respective cDNA of which transcription is controlled by CaMV 35S promoter and CaMV 35S terminator are connected in the order of CcF3'5'H, TorDFR, PhANS1, PhCHI1 and PhF3H1.

(14) Construction of pBS-35S-Del18

The pBS-35S-Del15 was cut with AscI, and a cohesive end was blunted with a Klenow fragment, followed by cutting with SphI to cut out a DNA fragment from the plasmid. This DNA fragment was inserted into a part formed by cutting the pBS-35S-UP4 with XbaI, and blunting a cohesive end with a Klenow fragment, followed by cutting with SphI to construct pBS-35S-Del18. The pBS-35S-Del18 is a plasmid wherein respective cDNA of which transcription is controlled by CaMV 35S promoter and CaMV 35S terminator are connected in the order of CcF3'5'H, FT, TorDFR, PhANS1, PhCHI1 and PhF3H1.

(15) Construction of pBIH-35S-Del8

The pBS-35S-Del8 was cut with SphI, a cohesive end was blunted with a Klenow fragment, followed by cutting with AscI to cut out a DNA fragment from the plasmid. This DNA fragment was inserted into a part formed by cutting pBI-SAS1 with AscI and SwaI, to construct pBIH-35S-Del8. The pBIH-35S-Del8 is a binary vector having a T-DNA region wherein HPT which is a selection marker and respective cDNA of which transcription is controlled by CaMV 35S promoter and CaMV 35S terminator are connected in the order of PhCHI1, PhF3H1, CcF3'5'H, TorANS and TorDFR.

(16) Construction of pBIH-35S-Del9

The pBS-35S-Del9 was cut with SphI, and a cohesive end was blunted with a Klenow fragment, followed by cutting with AscI to cut out a DNA fragment from the plasmid. This DNA fragment was inserted into a part formed by cutting pBI-SAS1 with AscI and SwaI, to construct pBIH-35S-Del9. The pBIH-35S-Del9 is a binary vector having a T-DNA region wherein HPT which is a selection marker and respective cDNA of which transcription is controlled by CaMV 35S promoter and CaMV 35S terminator are connected in the order of mPhCHS3, PhCHI1, PhF3H1, CcF3'5'H, TorANS and TorDFR.

(17) Construction of pBIH-35S-Del17

The pBS-35S-Del17 was cut with SphI, and a cohesive end was blunted with a Klenow fragment, followed by cutting with AscI to cut out a DNA fragment from the plasmid. This DNA fragment was inserted into a part formed by cutting pBI-SAS1 with AscI and SwaI, to construct pBIH-35S-Del17. The pBIH-35S-Del17 is a binary vector having a T-DNA region wherein HPT which is a selection marker and respective cDNA of which transcription is controlled by CaMV 35S promoter and CaMV 35S terminator are connected in the order of CcF3'5'H, TorDFR, PhANS1, PhCHI1 and PhF3H1.

(18) Construction of pBIH-35S-Del18

The pBS-35S-Del18 was cut with SphI, a cohesive end was blunted with a Klenow fragment, followed by cutting with AscI to cut out a DNA fragment from the plasmid. This DNA fragment was inserted into a part formed by cutting pBI-SAS1 with AscI and SwaI to construct pBIH-35S-Del18. The pBIH-35S-Del18 is a binary vector having a T-DNA region wherein HPT which is a selection marker and respective cDNA of which transcription is controlled by CaMV 35S promoter and CaMV 35S terminator are connected in the order of CcF3'5'H, FT, TorDFR, PhANS1, PhCHI1 and PhF3H1.

Example 25

Production of Transformed Moth Orchid

A transformed moth orchid produced by using DNA (pBIH-35S-CcF3'5'H, pBIH-35S-Del8, pBIH-35S-Del9, pBIH-35S-Del17 and pBIH-35S-Del18) which was constructed as binary vector in Example 24 and *Agrobacterium* EHA101 strain is selected with 50 mg/ml of hygromycin. As a result, a moth orchid wherein the genes shown in Example 24 are integrated into the chromosome could be obtained.

PLB can be induced from the obtained transformed moth orchid by using a part of plant such as flower stalk or axillary bud, and clone reproduction can be carried out. By carrying out cross-breeding using the obtained transformed moth orchid as a cross-breeding parent, it is possible to obtain a progeny having integrated genes.

Thus, by using the *Commelina communis* F3'5'H gene, a blue toned variety can be produced from an originally colored moth orchid, and a blue variety can be newly produced from a white moth orchid.

Example 26

Evaluation of Performance of the *Commelina communis* F3'5'H Gene on a Petal of *Cymbidium*

Ten pieces of a petal obtained from a bud having a length of 30 mm of a white *Cymbidium* (Cym. Lovely angel 'The Two Virgins') were cotransfected with one of the following three sets of genes in accordance with the method of Example 1.

(1) *Commelina communis* F3'5'H gene (CcF3'5'H)+Moth orchid CHS gene (PhCHS3)+Moth orchid CHI gene (PhCHI1)+Moth orchid F3H gene (PhF3H1)+*Gerbera* DFR gene (GerDFR)+*Gerbera* ANS gene (GerANS)

(2) Petunia F3'5'H2 gene (PetF3'5'H2)+Moth orchid CHS gene (PhCHS3)+Moth orchid CHI gene (PhCHI1)+Moth orchid F3H gene (PhF3H1)+*Gerbera* DFR gene (GerDFR)+*Gerbera* ANS gene (GerANS)

(3) Moth orchid CHS gene (PhCHS3)+Moth orchid CHI gene (PhCHI1)+Moth orchid F3H gene (PhF3H1)+*Gerbera* DFR gene (GerDFR)+*Gerbera* ANS gene (GerANS)

Figure 9:
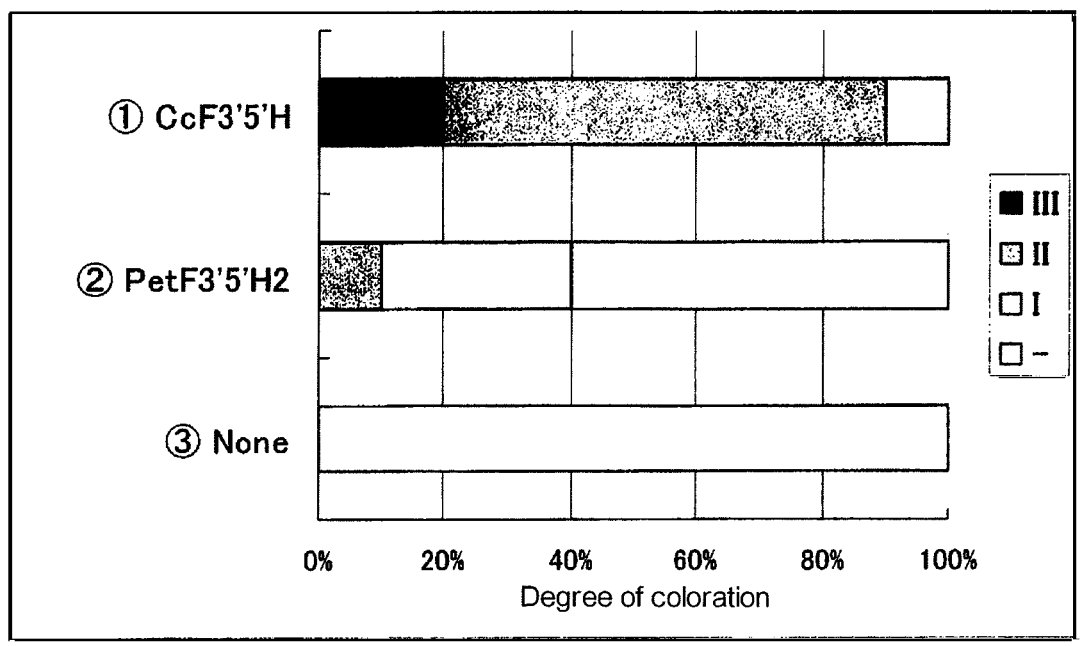
FIG. 9 is transfection of a petal of a white cymbidium with genes.

A transfected petal was static cultured for 5 days, and then observed by a stereomicroscope. Deep blue-purple cells newly emerged in the petals which was transfected with the gene set (1) including the *Commelina communis* F3'5'H gene (CcF3'5'H). On the other hand, in the petals which was transfected with the gene set (2) including the Petunia F3'5'H2 gene (PetF3'5'H2), light purple cells were observed only a part of the petals, and in the petals which was transfected with the gene set (3) containing no F3'5'H gene, flower color change was not observed at all. Results of evaluation of the degree of coloration of cells which emerged on each petal by the method described in Example 17 are shown on FIG. 9.

INDUSTRIAL APPLICABILITY

By using the *Commelina communis* F3'5'H gene, in addition to orchids having blue flowers which can not be accomplished by the conventional cross breeding methods, plants having various blue flower colors can be produced, and its applicability is extremely broad.

The entire disclosure of Japanese Patent Application No. 2007-066539 filed on Mar. 15, 2007 including specification, claims, drawings and summary is incorporated herein by reference in its entirety.

SEQUENCE LISTING

SEQ ID NO: 1, Nucleotide sequence encoding *Commelina communis* flavonoid 3',5'-hydroxylase
SEQ ID NO: 2, Amino acid sequence of *Commelina communis* flavonoid 3',5'-hydroxylase
SEQ ID NO: 3, Primer 35FH-1
SEQ ID NO: 4, Primer 35FH-4
SEQ ID NO: 5, Primer 35FH-2
SEQ ID NO: 6, Primer 35FH-3
SEQ ID NO: 7, Primer C35FH-3
SEQ ID NO: 8, Primer C35FH-4
SEQ ID NO: 9, Primer C35FH-6
SEQ ID NO: 10, Primer C35FH-5
SEQ ID NO: 11, Primer C35FH-7
SEQ ID NO: 12, Primer C35FH-10
SEQ ID NO: 13, Primer C35FH-9
SEQ ID NO: 14, Oligonucleotide SAS-S
SEQ ID NO: 15, Oligonucleotide SAS-AS
SEQ ID NO: 16, Primer T-CaMV35S-SseI-F
SEQ ID NO: 17, Primer T-CaMV35S-AscI-R
SEQ ID NO: 18, Primer CcF35H-F SEQ ID NO: 19, Primer CcF35H-R
SEQ ID NO: 20, Primer PetF3'5'H1-F
SEQ ID NO: 21, Primer PetF3'5'H1-R
SEQ ID NO: 22, Primer PetF3'5'H2-F
SEQ ID NO: 23, Primer PetF3'5'H2-R
SEQ ID NO: 24, Primer PhCHS3 F1
SEQ ID NO: 25, Primer PhCHS3 R1
SEQ ID NO: 26, Nucleotide sequence encoding *Doritaenopsis* hybrid cultivar chalcone synthase
SEQ ID NO: 27, Amino acid sequence of *Doritaenopsis* hybrid cultivar chalcone synthase
SEQ ID NO: 28, Primer CHI-dgF1
SEQ ID NO: 29, Primer CHI-dgR1
SEQ ID NO: 30, Primer CHI-dgF3
SEQ ID NO: 31, Primer CHI-dgR3
SEQ ID NO: 32, Primer PhCHI-GSP F1
SEQ ID NO: 33, Primer PhCHI-GSP F2
SEQ ID NO: 34, Primer PhCHI-GSP R1
SEQ ID NO: 35, Primer PhCHI-GSP R2
SEQ ID NO: 36, Primer PhCHI init
SEQ ID NO: 37, Primer PhCHI term
SEQ ID NO: 38, Nucleotide sequence encoding *Doritaenopsis* hybrid cultivar chalcone isomerase
SEQ ID NO: 39, Amino acid sequence of *Doritaenopsis* hybrid cultivar chalcone isomerase
SEQ ID NO: 40, Primer F3H-dgF1
SEQ ID NO: 41, Primer F3H-dgR1
SEQ ID NO: 42, Primer F3H-dgF3
SEQ ID NO: 43, Primer F3H-dgR3
SEQ ID NO: 44, Primer PhF3H-GSPF1
SEQ ID NO: 45, Primer PhF3H-GSPF2
SEQ ID NO: 46, Primer PhF3H-GSPR1
SEQ ID NO: 47, Primer PhF3H-GSPR2
SEQ ID NO: 48, Primer PhF3H init.
SEQ ID NO: 49, Primer PhF3H term.
SEQ ID NO: 50, Nucleotide sequence encoding *Doritaenopsis* hybrid cultivar flavanone 3-hydroxylase
SEQ ID NO: 51, Amino acid sequence of *Doritaenopsis* hybrid cultivar flavanone 3-hydroxylase
SEQ ID NO: 52, Primer DFRD-F1
SEQ ID NO: 53, Primer DFRD-R1
SEQ ID NO: 54, Primer DFRD-F2
SEQ ID NO: 55, Primer DFRD-R2
SEQ ID NO: 56, Primer DFRD-F3
SEQ ID NO: 57, Primer DFRD-R3
SEQ ID NO: 58, Primer PhDFR-F1
SEQ ID NO: 59, Primer PhDFR-F2
SEQ ID NO: 60, Primer PhDFR-R4
SEQ ID NO: 61, Primer PhDFR-R3
SEQ ID NO: 62, Primer PhDFR-F8A5
SEQ ID NO: 63, Primer PhDFR-R5
SEQ ID NO: 64, Nucleotide sequence encoding *Doritaenopsis* hybrid cultivar dihydroflavonol 4-reductase
SEQ ID NO: 65, Amino acid sequence of *Doritaenopsis* hybrid cultivar dihydroflavonol 4-reductase
SEQ ID NO: 66, Primer ANS-dgF2
SEQ ID NO: 67, Primer ANS-dgR2
SEQ ID NO: 68, Primer PhANS3RACEGSP1
SEQ ID NO: 69, Primer PhANS3RACEGSP2
SEQ ID NO: 70, Primer PhANS5RACEGSP1
SEQ ID NO: 71, Primer PhANS5RACEGSP2
SEQ ID NO: 72, Primer PhANS init
SEQ ID NO: 73, Primer PhANS term
SEQ ID NO: 74, Nucleotide sequence encoding *Doritaenopsis* hybrid cultivar anthocyanidin synthase
SEQ ID NO: 75, Amino acid sequence of *Doritaenopsis* hybrid cultivar anthocyanidin synthase
SEQ ID NO: 76, Primer GerDFR-F
SEQ ID NO: 77, Primer GerDFR-R
SEQ ID NO: 78, Primer GerANS-F
SEQ ID NO: 79, Primer GerANS-R
SEQ ID NO: 80, Primer TorDFR-F
SEQ ID NO: 81, Primer TorDFR-R
SEQ ID NO: 82, Primer TorANS-F
SEQ ID NO: 83, Primer TorANS-R
SEQ ID NO: 84, Primer AtFT 2nd-F
SEQ ID NO: 85, Primer AtFT 2nd-R
SEQ ID NO: 86, Primer PhCHS3-1038F
SEQ ID NO: 87, Primer PhCHS3-1073R

---

The invention claimed is:

1. An isolated gene encoding a flavonoid 3',5'-hydroxylase of *Commelina communis*, which flavonoid 3',5'-hydroxylase comprises the amino acid sequence depicted in SEQ ID No: 2 or an amino acid sequence having at least 98% homology to the amino acid sequence depicted in SEQ ID No: 2.

2. A vector, which contains the gene as defined in claim 1.

3. A method for producing a flower color-changed plant, which comprises transfecting a red moth orchid or a cymbidium with the gene as defined in claim 1 and expressing the gene.

4. A method for producing a flower color-changed plant, which comprises transfecting a moth orchid or a cymbidium with the gene as defined in claim 1 and a gene encoding a dihydroflavonol 4-reductase of *Torenia* or *Gerbera* and expressing the genes.

5. A method for producing an Orchid family plant having a blue flower, which comprises transfecting a moth orchid having a white flower with the gene as defined in claim 1, with a gene encoding a dihydroflavonol 4-reductase of *Torenia* or *Gerbera*, with a gene encoding a flavanone 3-hydroxylase, and with a gene encoding an anthocyanidin synthase and expressing the genes.

6. A flower color-changed plant or tissue thereof comprising the isolated gene encoding a flavonoid 3',5'-hydroxylase of *Commelina communis*, which is produced by the method as defined in claim 3.

7. A flower color-changed plant having the gene as defined in claim 1, which is a moth orchid or a cymbidium.

8. A flower color-changed plant or tissue thereof comprising the isolated gene encoding a flavonoid 3',5'-hydroxylase of *Commelina communis*, which is produced by the method as defined in claim 4.

9. A flower color-changed plant or a tissue thereof comprising the isolated gene encoding a flavonoid 3',5'-hydroxylase of *Commelina communis*, which is produced by the method as defined in claim 5.

* * * * *

SEQUENCE LISTING

```
<160> NUMBER OF SEQ ID NOS: 87

<210> SEQ ID NO 1
<211> LENGTH: 1524
<212> TYPE: DNA
<213> ORGANISM: Commelina communis
<220> FEATURE:
<221> NAME/KEY: CDS
<222> LOCATION: (1)..(1521)
<223> OTHER INFORMATION: Commelina communis flavonoid 3',5'-hydroxylase
      ( Cc F3'5'H )

<400> SEQUENCE: 1 atg gta ccc ctt acg tac ctt gca tgt ctc ctc ctc ccc ttc ctc ctc      48
Met Val Pro Leu Thr Tyr Leu Ala Cys Leu Leu Leu Pro Phe Leu Leu
1               5                   10                  15 cac cac ctc ctc ctc ctc cat cgc cga cgt cga ctc ccc ccc ggt ccc      96
His His Leu Leu Leu Leu His Arg Arg Arg Arg Leu Pro Pro Gly Pro
            20                  25                  30 ctc ggc ttc ccc atc cta ggc tcc ctc ccc tct ttg ggc acc acc cct     144
Leu Gly Phe Pro Ile Leu Gly Ser Leu Pro Ser Leu Gly Thr Thr Pro
        35                  40                  45 cac atc tct cta gct cat ctc tcc acc ctc tat ggc ccc att atg cac     192
```

```
                His Ile Ser Leu Ala His Leu Ser Thr Leu Tyr Gly Pro Ile Met His
                    50                  55                  60 ctt cga cta ggc caa gcc gat gtc gtc gtc gcc tcc acc ccc tcg gcc       240
Leu Arg Leu Gly Gln Ala Asp Val Val Val Ala Ser Thr Pro Ser Ala
65                  70                  75                  80 gcc cgt ctc ttc ctc aaa gac ctc gaa aac ttc ttt cgg gac cgt ccc       288
Ala Arg Leu Phe Leu Lys Asp Leu Glu Asn Phe Phe Arg Asp Arg Pro
                85                  90                  95 acc gat gct gca cca att cga tta gcc tat gaa gcc caa gac atg gtg       336
Thr Asp Ala Ala Pro Ile Arg Leu Ala Tyr Glu Ala Gln Asp Met Val
            100                 105                 110 ttt gca ccc tat ggc ccc aag tgg aag ctt ttg agg cgc cta gct cac       384
Phe Ala Pro Tyr Gly Pro Lys Trp Lys Leu Leu Arg Arg Leu Ala His
        115                 120                 125 caa gag atg cta ggg ccc aaa gca ctt gat aaa tgg agc tct ata aga       432
Gln Glu Met Leu Gly Pro Lys Ala Leu Asp Lys Trp Ser Ser Ile Arg
    130                 135                 140 tgt cgc gag gct gaa cgg atg gtc cgc tcg atg cgt agc tcg tcg gag       480
Cys Arg Glu Ala Glu Arg Met Val Arg Ser Met Arg Ser Ser Ser Glu
145                 150                 155                 160 tct ggg gag ctc gta aag gtg gca gag atg atg gtg ttt act att gct       528
Ser Gly Glu Leu Val Lys Val Ala Glu Met Met Val Phe Thr Ile Ala
                165                 170                 175 aac atg ata ggg agg gtt ata ctt agt agg aga gtg ttt gag gtg aag       576
Asn Met Ile Gly Arg Val Ile Leu Ser Arg Arg Val Phe Glu Val Lys
                180                 185                 190 gat ggg gag gct aat gag ttc aag gag atg gtg gtg gag ctg atg act       624
Asp Gly Glu Ala Asn Glu Phe Lys Glu Met Val Val Glu Leu Met Thr
            195                 200                 205 ttg gct ggg ctc ttt aac att ggg gac ttt gtt ccg gct gtg gcg tgg       672
Leu Ala Gly Leu Phe Asn Ile Gly Asp Phe Val Pro Ala Val Ala Trp
        210                 215                 220 atg gac ttg cag ggg ttg gag ggg aag atg aag aag ctg cat gtg agg       720
Met Asp Leu Gln Gly Leu Glu Gly Lys Met Lys Lys Leu His Val Arg
225                 230                 235                 240 ttc gat aag gtg ctc tcg aag ata ctg cga gag cac gag gcg acg aag       768
Phe Asp Lys Val Leu Ser Lys Ile Leu Arg Glu His Glu Ala Thr Lys
                245                 250                 255 ggg gag agg aag ggg agg gag gat tta ctt gat ctt ctg att gga tgc       816
Gly Glu Arg Lys Gly Arg Glu Asp Leu Leu Asp Leu Leu Ile Gly Cys
                260                 265                 270 aga gat gga cag gga ggg gag gag ggg gtg gag gtc act gat gat aat       864
Arg Asp Gly Gln Gly Gly Glu Glu Gly Val Glu Val Thr Asp Asp Asn
            275                 280                 285 atc aag gct gtc cta ttg aac tta ttc acg gcc ggt tct gac act tca       912
Ile Lys Ala Val Leu Leu Asn Leu Phe Thr Ala Gly Ser Asp Thr Ser
        290                 295                 300 act ggt gct ttg gag tgg gca ata acc gaa ctg ata gtg aac cca aca       960
Thr Gly Ala Leu Glu Trp Ala Ile Thr Glu Leu Ile Val Asn Pro Thr
305                 310                 315                 320 ata ctt cac aag gca caa gct gaa atg gac caa gtt atc gga cga aat      1008
Ile Leu His Lys Ala Gln Ala Glu Met Asp Gln Val Ile Gly Arg Asn
                325                 330                 335 cgc ctg ctc gaa gaa tcg gac ata ccg aag ttg cca tac cta aga gcc      1056
Arg Leu Leu Glu Glu Ser Asp Ile Pro Lys Leu Pro Tyr Leu Arg Ala
                340                 345                 350 ata gtg aag gaa aca ttc cga aaa cat cct tca aca cct tta aat ctc      1104
Ile Val Lys Glu Thr Phe Arg Lys His Pro Ser Thr Pro Leu Asn Leu
            355                 360                 365 cct cgt atc gca acc gaa gct tgt gaa gcc aat ggt tat tac att cca      1152
```

```
Pro Arg Ile Ala Thr Glu Ala Cys Glu Ala Asn Gly Tyr Tyr Ile Pro
        370                 375                 380 aag aac act aag ctc ttg gtc aac att tgg gca ata ggg cgt gac cca      1200
Lys Asn Thr Lys Leu Leu Val Asn Ile Trp Ala Ile Gly Arg Asp Pro
385                 390                 395                 400 aat gtt tgg cct aac cca ctc aaa ttt gac cca gaa cga ttt atg acc      1248
Asn Val Trp Pro Asn Pro Leu Lys Phe Asp Pro Glu Arg Phe Met Thr
            405                 410                 415 ttg aag ggc tct aaa att gac cca caa ggt aat gac ttt gag ctc ata      1296
Leu Lys Gly Ser Lys Ile Asp Pro Gln Gly Asn Asp Phe Glu Leu Ile
        420                 425                 430 cca ttc ggg tct gga cgc aga atc tgc gcc ggt gcc cgt atg ggt gtt      1344
Pro Phe Gly Ser Gly Arg Arg Ile Cys Ala Gly Ala Arg Met Gly Val
            435                 440                 445 gtg gtt gtg gag tac ctc ttg ggc ttg atg att cac gca ttt gac tgg      1392
Val Val Val Glu Tyr Leu Leu Gly Leu Met Ile His Ala Phe Asp Trp
        450                 455                 460 aaa ttg cct ctg ggt gaa acc atg gac atg ggc gag aca ttt gga atc      1440
Lys Leu Pro Leu Gly Glu Thr Met Asp Met Gly Glu Thr Phe Gly Ile
465                 470                 475                 480 gca ctt caa aag act gtg ccg gta gcg gca att gtg agc cct cgc cta      1488
Ala Leu Gln Lys Thr Val Pro Val Ala Ala Ile Val Ser Pro Arg Leu
            485                 490                 495 gag cca aac gtt tat aag aat ata aaa aca aca taa                       1524
Glu Pro Asn Val Tyr Lys Asn Ile Lys Thr Thr
        500                 505

<210> SEQ ID NO 2
<211> LENGTH: 507
<212> TYPE: PRT
<213> ORGANISM: Commelina communis

<400> SEQUENCE: 2

Met Val Pro Leu Thr Tyr Leu Ala Cys Leu Leu Leu Pro Phe Leu Leu
1               5                   10                  15

His His Leu Leu Leu Leu His Arg Arg Arg Leu Pro Pro Gly Pro
            20                  25                  30

Leu Gly Phe Pro Ile Leu Gly Ser Leu Pro Ser Leu Gly Thr Thr Pro
        35                  40                  45

His Ile Ser Leu Ala His Leu Ser Thr Leu Tyr Gly Pro Ile Met His
    50                  55                  60

Leu Arg Leu Gly Gln Ala Asp Val Val Ala Ser Thr Pro Ser Ala
65                  70                  75                  80

Ala Arg Leu Phe Leu Lys Asp Leu Glu Asn Phe Arg Asp Arg Pro
                85                  90                  95

Thr Asp Ala Ala Pro Ile Arg Leu Ala Tyr Glu Ala Gln Asp Met Val
            100                 105                 110

Phe Ala Pro Tyr Gly Pro Lys Trp Lys Leu Leu Arg Arg Leu Ala His
        115                 120                 125

Gln Glu Met Leu Gly Pro Lys Ala Leu Asp Lys Trp Ser Ser Ile Arg
    130                 135                 140

Cys Arg Glu Ala Glu Arg Met Val Arg Ser Met Arg Ser Ser Glu
145                 150                 155                 160

Ser Gly Glu Leu Val Lys Val Ala Glu Met Met Val Phe Thr Ile Ala
                165                 170                 175

Asn Met Ile Gly Arg Val Ile Leu Ser Arg Arg Val Phe Glu Val Lys
            180                 185                 190

Asp Gly Glu Ala Asn Glu Phe Lys Glu Met Val Val Glu Leu Met Thr
```

```
                195                 200                 205
Leu Ala Gly Leu Phe Asn Ile Gly Asp Phe Val Pro Ala Val Ala Trp
210                 215                 220

Met Asp Leu Gln Gly Leu Glu Gly Lys Met Lys Leu His Val Arg
225                 230                 235                 240

Phe Asp Lys Val Leu Ser Lys Ile Leu Arg Glu His Glu Ala Thr Lys
                245                 250                 255

Gly Glu Arg Lys Gly Arg Glu Asp Leu Leu Asp Leu Leu Ile Gly Cys
                260                 265                 270

Arg Asp Gly Gln Gly Gly Glu Glu Gly Val Glu Val Thr Asp Asp Asn
                275                 280                 285

Ile Lys Ala Val Leu Leu Asn Leu Phe Thr Ala Gly Ser Asp Thr Ser
                290                 295                 300

Thr Gly Ala Leu Glu Trp Ala Ile Thr Glu Leu Ile Val Asn Pro Thr
305                 310                 315                 320

Ile Leu His Lys Ala Gln Ala Glu Met Asp Gln Val Ile Gly Arg Asn
                325                 330                 335

Arg Leu Leu Glu Glu Ser Asp Ile Pro Lys Leu Pro Tyr Leu Arg Ala
                340                 345                 350

Ile Val Lys Glu Thr Phe Arg Lys His Pro Ser Thr Pro Leu Asn Leu
                355                 360                 365

Pro Arg Ile Ala Thr Glu Ala Cys Glu Ala Asn Gly Tyr Tyr Ile Pro
                370                 375                 380

Lys Asn Thr Lys Leu Leu Val Asn Ile Trp Ala Ile Gly Arg Asp Pro
385                 390                 395                 400

Asn Val Trp Pro Asn Pro Leu Lys Phe Asp Pro Glu Arg Phe Met Thr
                405                 410                 415

Leu Lys Gly Ser Lys Ile Asp Pro Gln Gly Asn Asp Phe Glu Leu Ile
                420                 425                 430

Pro Phe Gly Ser Gly Arg Arg Ile Cys Ala Gly Ala Arg Met Gly Val
                435                 440                 445

Val Val Val Glu Tyr Leu Leu Gly Leu Met Ile His Ala Phe Asp Trp
450                 455                 460

Lys Leu Pro Leu Gly Glu Thr Met Asp Met Gly Glu Thr Phe Gly Ile
465                 470                 475                 480

Ala Leu Gln Lys Thr Val Pro Val Ala Ala Ile Val Ser Pro Arg Leu
                485                 490                 495

Glu Pro Asn Val Tyr Lys Asn Ile Lys Thr Thr
                500                 505

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (6)..(6)
<223> OTHER INFORMATION: Inosine
<220> FEATURE:
<221> NAME/KEY: modified_base
<222> LOCATION: (9)..(9)
<223> OTHER INFORMATION: Inosine
<220> FEATURE:
<221> NAME/KEY: modified_base
<222> LOCATION: (15)..(15)
<223> OTHER INFORMATION: Inosine
```

-continued

```
<400> SEQUENCE: 3
atggtngtng arytnatgac                                                 20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (6)..(6)
<223> OTHER INFORMATION: Inosine
<220> FEATURE:
<221> NAME/KEY: modified_base
<222> LOCATION: (9)..(9)
<223> OTHER INFORMATION: Inosine
<220> FEATURE:
<221> NAME/KEY: modified_base
<222> LOCATION: (12)..(12)
<223> OTHER INFORMATION: Inosine

<400> SEQUENCE: 4
ccraanggna tnarytcraa                                                 20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (12)..(12)
<223> OTHER INFORMATION: Inosine
<220> FEATURE:
<221> NAME/KEY: modified_base
<222> LOCATION: (18)..(18)
<223> OTHER INFORMATION: Inosine

<400> SEQUENCE: 5
tggatggayy tncarggnat                                                 20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (6)..(6)
<223> OTHER INFORMATION: Inosine
<220> FEATURE:
<221> NAME/KEY: modified_base
<222> LOCATION: (18)..(18)
<223> OTHER INFORMATION: Inosine

<400> SEQUENCE: 6
ccdatngccc adatrttnac                                                 20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 7
atctccctcg tatcgcaacc                                        20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gaagcttgtg aagccaatgg                                        20

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cgtcgcctcg tgctctcgca gtatc                                  25

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tcttcgagag caccttatcg aacctc                                 26

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gaaaaccaat acaaaaacat acc                                    23

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
attgcttcaa gttccctagc                                        20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13

```
gttccctagc cccgtaccac                                                     20

<210> SEQ ID NO 14
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ctagctagcg gcgcgcctgc aggatatcat ttaaatcccg gg                             42

<210> SEQ ID NO 15
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
cccgggattt aaatgatatc ctgcaggcgc gccgctagct ag                             42

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
aacctgcagg aaatcaccag tctctctcta                                          30

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ggcgcgccat cgataagggg ttattag                                             27

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
atggtacccc ttacgtacct t                                                   21

<210> SEQ ID NO 19
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ttatgttgtt tttatattct tataaacg                                            28
```

```
<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
atgatgctac ttactgagct tggtg                                        25

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
caacatgcgc aattatagca                                              20

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
atggtgctac ttagtgagct tgc                                          23

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
aaccaacgta aaggcatgtt                                              20

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
aagcttgtga gagacgacgg a                                            21

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tggccctaat ccttcaaatt                                              20

<210> SEQ ID NO 26
```

```
<211> LENGTH: 1185
<212> TYPE: DNA
<213> ORGANISM: Doritaenopsis hybrid cultivar
<220> FEATURE:
<221> NAME/KEY: CDS
<222> LOCATION: (1)..(1182)
<223> OTHER INFORMATION: Doritaenopsis hybrid cultivar chalcone synthase
      (PhCHS 3)

<400> SEQUENCE: 26
```

| | | | | | | | | | | | | | | | | |
|---|---|---|---|---|---|---|---|---|---|---|---|---|---|---|---|---|
| atg | gcg | ccg | gcg | atg | gag | gag | atc | agg | cga | act | cag | aga | gct | gag | ggc | 48 |
| Met | Ala | Pro | Ala | Met | Glu | Glu | Ile | Arg | Arg | Thr | Gln | Arg | Ala | Glu | Gly | |
| 1 | | | | 5 | | | | | 10 | | | | | 15 | | |
| ccc | gcg | gcg | gtg | ctc | gca | atc | ggc | acc | tcc | acg | ccg | ccg | aac | gct | ctg | 96 |
| Pro | Ala | Ala | Val | Leu | Ala | Ile | Gly | Thr | Ser | Thr | Pro | Pro | Asn | Ala | Leu | |
| | | 20 | | | | | 25 | | | | | 30 | | | | |
| tat | cag | gcc | gat | tat | ccc | gat | tat | tac | ttc | aga | atc | acc | aac | tgc | gag | 144 |
| Tyr | Gln | Ala | Asp | Tyr | Pro | Asp | Tyr | Tyr | Phe | Arg | Ile | Thr | Asn | Cys | Glu | |
| | | | 35 | | | | | 40 | | | | | 45 | | | |
| cat | ctc | act | gac | ctc | aag | gag | aag | ttc | aag | cga | atg | tgc | gag | aaa | tcc | 192 |
| His | Leu | Thr | Asp | Leu | Lys | Glu | Lys | Phe | Lys | Arg | Met | Cys | Glu | Lys | Ser | |
| 50 | | | | | 55 | | | | | 60 | | | | | | |
| atg | ata | aaa | aaa | cgg | tac | atg | tat | cta | aca | gaa | gaa | ttc | ctg | aaa | gaa | 240 |
| Met | Ile | Lys | Lys | Arg | Tyr | Met | Tyr | Leu | Thr | Glu | Glu | Phe | Leu | Lys | Glu | |
| 65 | | | | 70 | | | | | 75 | | | | | 80 | | |
| aat | ccc | aat | atc | tgc | gca | ttc | atg | gct | cct | tca | ctc | gac | gcc | cgg | caa | 288 |
| Asn | Pro | Asn | Ile | Cys | Ala | Phe | Met | Ala | Pro | Ser | Leu | Asp | Ala | Arg | Gln | |
| | | | 85 | | | | | 90 | | | | | 95 | | | |
| gac | ata | gtt | gtc | gcc | gag | gtc | ccg | aag | ctc | gcc | aaa | gag | gcc | gcc | gcg | 336 |
| Asp | Ile | Val | Val | Ala | Glu | Val | Pro | Lys | Leu | Ala | Lys | Glu | Ala | Ala | Ala | |
| | | 100 | | | | | 105 | | | | | 110 | | | | |
| cgc | gcc | atc | aag | gaa | tgg | gga | cac | ccc | aaa | tca | cgc | ata | act | cat | ctc | 384 |
| Arg | Ala | Ile | Lys | Glu | Trp | Gly | His | Pro | Lys | Ser | Arg | Ile | Thr | His | Leu | |
| | 115 | | | | | 120 | | | | | 125 | | | | | |
| atc | ttc | tgc | acc | acc | agc | ggc | gtc | gac | atg | ccc | ggc | gcc | gac | tac | caa | 432 |
| Ile | Phe | Cys | Thr | Thr | Ser | Gly | Val | Asp | Met | Pro | Gly | Ala | Asp | Tyr | Gln | |
| | 130 | | | | | 135 | | | | | 140 | | | | | |
| ctc | acc | cgc | ctc | ctc | ggt | ctc | cgc | ccc | tcc | gtc | aac | aga | ttc | atg | ctc | 480 |
| Leu | Thr | Arg | Leu | Leu | Gly | Leu | Arg | Pro | Ser | Val | Asn | Arg | Phe | Met | Leu | |
| 145 | | | | | 150 | | | | | 155 | | | | | 160 | |
| tac | cag | cag | ggc | tgc | ttc | gcc | ggc | ggc | acc | gtc | ctc | cgc | ctc | gcc | aag | 528 |
| Tyr | Gln | Gln | Gly | Cys | Phe | Ala | Gly | Gly | Thr | Val | Leu | Arg | Leu | Ala | Lys | |
| | | | 165 | | | | | 170 | | | | | 175 | | | |
| gat | ctc | gcc | gag | aac | aac | gcc | ggc | gcc | cgc | gtg | ctc | gtc | gtt | tgc | tcc | 576 |
| Asp | Leu | Ala | Glu | Asn | Asn | Ala | Gly | Ala | Arg | Val | Leu | Val | Val | Cys | Ser | |
| | | | | 180 | | | | | 185 | | | | | 190 | | |
| gaa | atc | acc | gcc | gtc | act | ttc | cgc | ggc | ccg | tcg | gaa | tcc | cat | ctc | gat | 624 |
| Glu | Ile | Thr | Ala | Val | Thr | Phe | Arg | Gly | Pro | Ser | Glu | Ser | His | Leu | Asp | |
| | | | 195 | | | | | 200 | | | | | 205 | | | |
| tcc | ctc | gtc | gga | cag | gcg | ctc | ttc | ggc | gac | ggc | gcc | gcc | gct | atc | att | 672 |
| Ser | Leu | Val | Gly | Gln | Ala | Leu | Phe | Gly | Asp | Gly | Ala | Ala | Ala | Ile | Ile | |
| | 210 | | | | | 215 | | | | | 220 | | | | | |
| gtc | gga | tcc | gac | cct | gat | tta | gcc | acc | gag | cgc | cct | ctg | ttt | caa | cta | 720 |
| Val | Gly | Ser | Asp | Pro | Asp | Leu | Ala | Thr | Glu | Arg | Pro | Leu | Phe | Gln | Leu | |
| 225 | | | | | 230 | | | | | 235 | | | | | 240 | |
| gtc | tct | gct | tcc | caa | acc | atc | ctt | ccc | gaa | tca | gag | ggc | gcc | att | gat | 768 |
| Val | Ser | Ala | Ser | Gln | Thr | Ile | Leu | Pro | Glu | Ser | Glu | Gly | Ala | Ile | Asp | |
| | | | | 245 | | | | | 250 | | | | | 255 | | |
| ggc | cac | ctt | cgt | gaa | atc | ggg | ctc | acc | ttc | cac | cta | ctc | aaa | gac | gtc | 816 |
| Gly | His | Leu | Arg | Glu | Ile | Gly | Leu | Thr | Phe | His | Leu | Leu | Lys | Asp | Val | |
| | | | | 260 | | | | | 265 | | | | | 270 | | |
| ccc | ggc | ctc | att | tct | aaa | aac | att | caa | aaa | tgt | ctc | ctt | gag | gcc | ttc | 864 |

```
Pro Gly Leu Ile Ser Lys Asn Ile Gln Lys Cys Leu Leu Glu Ala Phe
            275                 280                 285 aag cca ctt ggt gtg ctt gat tgg aac tct att ttt tgg atc gct cac      912
Lys Pro Leu Gly Val Leu Asp Trp Asn Ser Ile Phe Trp Ile Ala His
        290                 295                 300 ccg ggc ggc ccg gct ata ctc gat caa gtt gag acc aag ctc ggt cta      960
Pro Gly Gly Pro Ala Ile Leu Asp Gln Val Glu Thr Lys Leu Gly Leu
305                 310                 315                 320 aag tcc gag aag ctc gcc gcg agt aga aat gtg ctc gct gac tac ggt     1008
Lys Ser Glu Lys Leu Ala Ala Ser Arg Asn Val Leu Ala Asp Tyr Gly
                325                 330                 335 aac atg tcg agc gca tgc gtt ctt ttc ata ctc gat gag atg cga agg     1056
Asn Met Ser Ser Ala Cys Val Leu Phe Ile Leu Asp Glu Met Arg Arg
            340                 345                 350 cga tcg gca gag gct ggg cag tcg acc act ggc gag ggt ttg gag tgg     1104
Arg Ser Ala Glu Ala Gly Gln Ser Thr Thr Gly Glu Gly Leu Glu Trp
        355                 360                 365 gga gtt cta ttc ggg ttc ggt ccg gga ctt acg gtc gag act gtt gta     1152
Gly Val Leu Phe Gly Phe Gly Pro Gly Leu Thr Val Glu Thr Val Val
370                 375                 380 tta cgc agc gtt ccg att ggt ggc acc gag taa                         1185
Leu Arg Ser Val Pro Ile Gly Gly Thr Glu
385                 390
```

<210> SEQ ID NO 27
<211> LENGTH: 394
<212> TYPE: PRT
<213> ORGANISM: Doritaenopsis hybrid cultivar

<400> SEQUENCE: 27

```
Met Ala Pro Ala Met Glu Glu Ile Arg Arg Thr Gln Arg Ala Glu Gly
1               5                   10                  15

Pro Ala Ala Val Leu Ala Ile Gly Thr Ser Thr Pro Pro Asn Ala Leu
            20                  25                  30

Tyr Gln Ala Asp Tyr Pro Asp Tyr Tyr Phe Arg Ile Thr Asn Cys Glu
        35                  40                  45

His Leu Thr Asp Leu Lys Glu Lys Phe Lys Arg Met Cys Glu Lys Ser
    50                  55                  60

Met Ile Lys Lys Arg Tyr Met Tyr Leu Thr Glu Glu Phe Leu Lys Glu
65                  70                  75                  80

Asn Pro Asn Ile Cys Ala Phe Met Ala Pro Ser Leu Asp Ala Arg Gln
                85                  90                  95

Asp Ile Val Val Ala Glu Val Pro Lys Leu Ala Lys Glu Ala Ala Ala
            100                 105                 110

Arg Ala Ile Lys Glu Trp Gly His Pro Lys Ser Arg Ile Thr His Leu
        115                 120                 125

Ile Phe Cys Thr Thr Ser Gly Val Asp Met Pro Gly Ala Asp Tyr Gln
    130                 135                 140

Leu Thr Arg Leu Leu Gly Leu Arg Pro Ser Val Asn Arg Phe Met Leu
145                 150                 155                 160

Tyr Gln Gln Gly Cys Phe Ala Gly Gly Thr Val Leu Arg Leu Ala Lys
                165                 170                 175

Asp Leu Ala Glu Asn Asn Ala Gly Ala Arg Val Leu Val Val Cys Ser
            180                 185                 190

Glu Ile Thr Ala Val Thr Phe Arg Gly Pro Ser Glu Ser His Leu Asp
        195                 200                 205

Ser Leu Val Gly Gln Ala Leu Phe Gly Asp Gly Ala Ala Ala Ile Ile
    210                 215                 220
```

Val Gly Ser Asp Pro Asp Leu Ala Thr Glu Arg Pro Leu Phe Gln Leu
225                 230                 235                 240

Val Ser Ala Ser Gln Thr Ile Leu Pro Glu Ser Glu Gly Ala Ile Asp
            245                 250                 255

Gly His Leu Arg Glu Ile Gly Leu Thr Phe His Leu Leu Lys Asp Val
        260                 265                 270

Pro Gly Leu Ile Ser Lys Asn Ile Gln Lys Cys Leu Leu Glu Ala Phe
    275                 280                 285

Lys Pro Leu Gly Val Leu Asp Trp Asn Ser Ile Phe Trp Ile Ala His
290                 295                 300

Pro Gly Gly Pro Ala Ile Leu Asp Gln Val Glu Thr Lys Leu Gly Leu
305                 310                 315                 320

Lys Ser Glu Lys Leu Ala Ala Ser Arg Asn Val Leu Ala Asp Tyr Gly
            325                 330                 335

Asn Met Ser Ser Ala Cys Val Leu Phe Ile Leu Asp Glu Met Arg Arg
        340                 345                 350

Arg Ser Ala Glu Ala Gly Gln Ser Thr Thr Gly Glu Gly Leu Glu Trp
    355                 360                 365

Gly Val Leu Phe Gly Phe Gly Pro Gly Leu Thr Val Glu Thr Val Val
370                 375                 380

Leu Arg Ser Val Pro Ile Gly Gly Thr Glu
385                 390

<210> SEQ ID NO 28
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ttyctcgsyg gbgcmggygw vmgvgg                                          26

<210> SEQ ID NO 29
<211> LENGTH: 28
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (5)..(5)
<223> OTHER INFORMATION: Inosine
<220> FEATURE:
<221> NAME/KEY: modified_base
<222> LOCATION: (8)..(8)
<223> OTHER INFORMATION: Inosine
<220> FEATURE:
<221> NAME/KEY: modified_base
<222> LOCATION: (20)..(20)
<223> OTHER INFORMATION: Inosine

<400> SEQUENCE: 29
cmggnganac vscrtkytyn ccratvat                                        28

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

```
<220> FEATURE:
<221> NAME/KEY: modified_base
<222> LOCATION: (3)..(3)
<223> OTHER INFORMATION: Inosine
<220> FEATURE:
<221> NAME/KEY: modified_base
<222> LOCATION: (11)..(11)
<223> OTHER INFORMATION: Inosine
<220> FEATURE:
<221> NAME/KEY: modified_base
<222> LOCATION: (14)..(14)
<223> OTHER INFORMATION: Inosine

<400> SEQUENCE: 30
tmnkywcmgg nsmnttygar aaryt                                          25

<210> SEQ ID NO 31
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (3)..(3)
<223> OTHER INFORMATION: Inosine
<220> FEATURE:
<221> NAME/KEY: modified_base
<222> LOCATION: (12)..(12)
<223> OTHER INFORMATION: Inosine
<220> FEATURE:
<221> NAME/KEY: modified_base
<222> LOCATION: (21)..(21)
<223> OTHER INFORMATION: Inosine

<400> SEQUENCE: 31
tynccratva tngwhtccar naybgc                                         26

<210> SEQ ID NO 32
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
atgctgctgc cattaacggg tca                                            23

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
tccgagaagg tctccgggaa ct                                             22

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gcattcgtca gcttcttgct ctct                                           24
```

-continued

```
<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
atcacatcag tctcagccac a                                              21

<210> SEQ ID NO 36
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
atggcagaaa cagtggcgac gccca                                          25

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
tcaaacgact ccatcttgct c                                              21

<210> SEQ ID NO 38
<211> LENGTH: 723
<212> TYPE: DNA
<213> ORGANISM: Doritaenopsis hybrid cultivar
<220> FEATURE:
<221> NAME/KEY: CDS
<222> LOCATION: (1)..(720)
<223> OTHER INFORMATION: Doritaenopsis hybrid cultivar chalcone isomerase
      ( PhCHI 3 )

<400> SEQUENCE: 38 atg gca gaa aca gtg gcg acg ccc atc gag gtg gag gga gtg aag ttt     48
Met Ala Glu Thr Val Ala Thr Pro Ile Glu Val Glu Gly Val Lys Phe
1               5                   10                  15 ccg gcc gag atc tcg tcg ccg gcg acc tcg aaa cct cta ttt ctc ggt     96
Pro Ala Glu Ile Ser Ser Pro Ala Thr Ser Lys Pro Leu Phe Leu Gly
            20                  25                  30 ggc gca ggg gcg agg ggt ata gaa gtt gga gga aag ttt tta gcc gta    144
Gly Ala Gly Ala Arg Gly Ile Glu Val Gly Gly Lys Phe Leu Ala Val
        35                  40                  45 acc gcg atc gga gtg tac ttg gaa gcg gcg gtg att ccg gcg atc gcc    192
Thr Ala Ile Gly Val Tyr Leu Glu Ala Ala Val Ile Pro Ala Ile Ala
    50                  55                  60 gga aaa tgg acg ggg aag aag gcg gag aag ctc act gat tcg gtt gac    240
Gly Lys Trp Thr Gly Lys Lys Ala Glu Lys Leu Thr Asp Ser Val Asp
65                  70                  75                  80 ttt tac cga gac att att aca ggt tcc ttt gag aag ctg acg aga gtg    288
Phe Tyr Arg Asp Ile Ile Thr Gly Ser Phe Glu Lys Leu Thr Arg Val
                85                  90                  95 acg atg ctg ctg cca tta acg ggt caa cag tac tcc gag aag gtc tcc    336
Thr Met Leu Leu Pro Leu Thr Gly Gln Gln Tyr Ser Glu Lys Val Ser
            100                 105                 110
```

-continued

```
ggg aac tgc gtc gcc gca tgg aaa gcc gcc gga gaa tac aca gag gaa      384
Gly Asn Cys Val Ala Ala Trp Lys Ala Ala Gly Glu Tyr Thr Glu Glu
            115                 120                 125 gaa gca acg gcc att aat aag ttt ctg gaa atc ttc aag cct aag aac      432
Glu Ala Thr Ala Ile Asn Lys Phe Leu Glu Ile Phe Lys Pro Lys Asn
    130                 135                 140 ttt ctt cca ggc acc tcc atc atc ttc act cat tcc cct cat ggc tct      480
Phe Leu Pro Gly Thr Ser Ile Ile Phe Thr His Ser Pro His Gly Ser
145                 150                 155                 160 ctc act att gga ttt ttg gag ggg gat ggc gtt cct gtg gct gag act      528
Leu Thr Ile Gly Phe Leu Glu Gly Asp Gly Val Pro Val Ala Glu Thr
                165                 170                 175 gat gtg ata gag agc aag aag ctg acg aat gcg gtg ttg gaa tcc att      576
Asp Val Ile Glu Ser Lys Lys Leu Thr Asn Ala Val Leu Glu Ser Ile
            180                 185                 190 ata ggg gag aat gga gtt tct ccc gct gcg aaa cag agc ctg gct cgg      624
Ile Gly Glu Asn Gly Val Ser Pro Ala Ala Lys Gln Ser Leu Ala Arg
        195                 200                 205 agg ttt tca gag ctt ctg aat aag aaa gaa gac caa gaa gaa gaa gat      672
Arg Phe Ser Glu Leu Leu Asn Lys Lys Glu Asp Gln Glu Glu Glu Asp
    210                 215                 220 ggg att ttg gat gtg gag aaa gcc aaa tta gag caa gat gga gtc gtt      720
Gly Ile Leu Asp Val Glu Lys Ala Lys Leu Glu Gln Asp Gly Val Val
225                 230                 235                 240 tga                                                                    723
```

```
<210> SEQ ID NO 39
<211> LENGTH: 240
<212> TYPE: PRT
<213> ORGANISM: Doritaenopsis hybrid cultivar

<400> SEQUENCE: 39
```

Met Ala Glu Thr Val Ala Thr Pro Ile Glu Val Glu Gly Val Lys Phe
1               5                   10                  15

Pro Ala Glu Ile Ser Ser Pro Ala Thr Ser Lys Pro Leu Phe Leu Gly
                20                  25                  30

Gly Ala Gly Ala Arg Gly Ile Glu Val Gly Gly Lys Phe Leu Ala Val
            35                  40                  45

Thr Ala Ile Gly Val Tyr Leu Glu Ala Ala Val Ile Pro Ala Ile Ala
        50                  55                  60

Gly Lys Trp Thr Gly Lys Lys Ala Glu Lys Leu Thr Asp Ser Val Asp
65                  70                  75                  80

Phe Tyr Arg Asp Ile Ile Thr Gly Ser Phe Glu Lys Leu Thr Arg Val
                85                  90                  95

Thr Met Leu Leu Pro Leu Thr Gly Gln Gln Tyr Ser Glu Lys Val Ser
                100                 105                 110

Gly Asn Cys Val Ala Ala Trp Lys Ala Ala Gly Glu Tyr Thr Glu Glu
            115                 120                 125

Glu Ala Thr Ala Ile Asn Lys Phe Leu Glu Ile Phe Lys Pro Lys Asn
    130                 135                 140

Phe Leu Pro Gly Thr Ser Ile Ile Phe Thr His Ser Pro His Gly Ser
145                 150                 155                 160

Leu Thr Ile Gly Phe Leu Glu Gly Asp Gly Val Pro Val Ala Glu Thr
                165                 170                 175

Asp Val Ile Glu Ser Lys Lys Leu Thr Asn Ala Val Leu Glu Ser Ile
            180                 185                 190

Ile Gly Glu Asn Gly Val Ser Pro Ala Ala Lys Gln Ser Leu Ala Arg

```
                195                 200                 205
Arg Phe Ser Glu Leu Leu Asn Lys Lys Glu Asp Gln Glu Glu Glu Asp
    210                 215                 220

Gly Ile Leu Asp Val Glu Lys Ala Lys Leu Glu Gln Asp Gly Val Val
225                 230                 235                 240
```

<210> SEQ ID NO 40
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (2)..(2)
<223> OTHER INFORMATION: Inosine
<220> FEATURE:
<221> NAME/KEY: modified_base
<222> LOCATION: (5)..(5)
<223> OTHER INFORMATION: Inosine
<220> FEATURE:
<221> NAME/KEY: modified_base
<222> LOCATION: (23)..(23)
<223> OTHER INFORMATION: Inosine

<400> SEQUENCE: 40
tnvgngayga rgabgarmgb ccnaa                                            25

<210> SEQ ID NO 41
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
acbgcyygrt grtchgcrtt cttraa                                           26

<210> SEQ ID NO 42
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (24)..(24)
<223> OTHER INFORMATION: Inosine

<400> SEQUENCE: 42
aarytbrgkt tygayatgwc hggng                                            25

<210> SEQ ID NO 43
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (18)..(18)
<223> OTHER INFORMATION: Inosine

<400> SEQUENCE: 43
gghwsracvg tdatccangw btt                                              23

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
ttctcatacc caatcgggag                                                   20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
aatcgggagc cgcgattact                                                   20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
tctgtgtggc gcttcaggcc                                                   20

<210> SEQ ID NO 47
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
tgaggtccgg ttgcgggcat ttt                                               23

<210> SEQ ID NO 48
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
atggccccaa taccattcct accga                                             25

<210> SEQ ID NO 49
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
ccttaagcta aaatctcatt taatgccttt gctcc                                  35

<210> SEQ ID NO 50

<211> LENGTH: 1113
<212> TYPE: DNA
<213> ORGANISM: Doritaenopsis hybrid cultivar
<220> FEATURE:
<221> NAME/KEY: CDS
<222> LOCATION: (1)..(1110)
<223> OTHER INFORMATION: Doritaenopsis hybrid cultivar flavanone
3-hydroxylase ( PhF3H 1 )

<400> SEQUENCE: 50

```
atg gcc cca ata cca ttc cta ccg act gcg gtt aca gag aag aca ctg      48
Met Ala Pro Ile Pro Phe Leu Pro Thr Ala Val Thr Glu Lys Thr Leu
1               5                   10                  15 aga gca agc ttt gta cgg gat gag gac gag agg cca aag gta gcc tac      96
Arg Ala Ser Phe Val Arg Asp Glu Asp Glu Arg Pro Lys Val Ala Tyr
            20                  25                  30 aac gaa ttc agt aac cag att ccg gtg atc tca ctt cag ggg atc gaa     144
Asn Glu Phe Ser Asn Gln Ile Pro Val Ile Ser Leu Gln Gly Ile Glu
        35                  40                  45 gag aat gga gac gga ggt cga agg tcg gag att tgc cgg agt atc gtg     192
Glu Asn Gly Asp Gly Gly Arg Arg Ser Glu Ile Cys Arg Ser Ile Val
    50                  55                  60 gca gcg tgc gag gac tgg gga atc ttt cag gcc gtc gac cat ggt gtc     240
Ala Ala Cys Glu Asp Trp Gly Ile Phe Gln Ala Val Asp His Gly Val
65                  70                  75                  80 gat gca ggg ctc atc gca gac atg aac cgc ctt gct cga gag ttc ttc     288
Asp Ala Gly Leu Ile Ala Asp Met Asn Arg Leu Ala Arg Glu Phe Phe
                85                  90                  95 gat ctg ctg cca gag gag aag ctt cgt ttt gac atg tcc ggc ggg aag     336
Asp Leu Leu Pro Glu Glu Lys Leu Arg Phe Asp Met Ser Gly Gly Lys
            100                 105                 110 aaa ggc ggc ttc atc gtt tcc agc cat ctt cag ggt gaa gta gtt caa     384
Lys Gly Gly Phe Ile Val Ser Ser His Leu Gln Gly Glu Val Val Gln
        115                 120                 125 gat tgg agg gag atc gtt acc tat ttc tca tac cca atc ggg agc cgc     432
Asp Trp Arg Glu Ile Val Thr Tyr Phe Ser Tyr Pro Ile Gly Ser Arg
    130                 135                 140 gat tac tcg cgg tgg ccg gac aag ccg gag ggg tgg cgc gct gtt gtg     480
Asp Tyr Ser Arg Trp Pro Asp Lys Pro Glu Gly Trp Arg Ala Val Val
145                 150                 155                 160 gag gag tac agc gcc aag ctg atg gag ctg gcc tgc aat ctc ctc ggc     528
Glu Glu Tyr Ser Ala Lys Leu Met Glu Leu Ala Cys Asn Leu Leu Gly
                165                 170                 175 gtg cta tcg gaa gcc atg gga cta gat cgt gaa gcc cta gcc gga gcc     576
Val Leu Ser Glu Ala Met Gly Leu Asp Arg Glu Ala Leu Ala Gly Ala
            180                 185                 190 tgt atc gat atg gac cag aaa ttg gtg gtc aat ttc tac cca aaa tgc     624
Cys Ile Asp Met Asp Gln Lys Leu Val Val Asn Phe Tyr Pro Lys Cys
        195                 200                 205 ccg caa ccg gac ctc acc ctg ggc ctg aag cgc cac aca gac ccc ggc     672
Pro Gln Pro Asp Leu Thr Leu Gly Leu Lys Arg His Thr Asp Pro Gly
    210                 215                 220 acc att acc ctg ttg ctt caa gat caa gtc ggc ggt ctc caa gcc acc     720
Thr Ile Thr Leu Leu Leu Gln Asp Gln Val Gly Gly Leu Gln Ala Thr
225                 230                 235                 240 aag gac gac ggt aaa acc tgg atc acc gtt cag cct gtc cag aat gct     768
Lys Asp Asp Gly Lys Thr Trp Ile Thr Val Gln Pro Val Gln Asn Ala
                245                 250                 255 ttc gtc gtt aac ctc ggc gac cac ggt cat tac ctg agc aac ggt cgg     816
Phe Val Val Asn Leu Gly Asp His Gly His Tyr Leu Ser Asn Gly Arg
            260                 265                 270 ttt aag aac gcg gac cat cag gcc gtc gtg aac tcg aat tac agc cgg     864
Phe Lys Asn Ala Asp His Gln Ala Val Val Asn Ser Asn Tyr Ser Arg
```

```
                Phe Lys Asn Ala Asp His Gln Ala Val Val Asn Ser Asn Tyr Ser Arg
                    275                 280                 285 ctt tcg atc gcg gcg ttc cag aac cct gct ccg gaa gcg gtt gtt tac        912
Leu Ser Ile Ala Ala Phe Gln Asn Pro Ala Pro Glu Ala Val Val Tyr
    290                 295                 300 ccg cta gcg gtg agg gaa gga gag agg ccg gtg atg gag gag ggc atc        960
Pro Leu Ala Val Arg Glu Gly Glu Arg Pro Val Met Glu Glu Gly Ile
305                 310                 315                 320 aca ttt gcg gag atg tat agg agg aag atg agc agg gat ctg gag ctg       1008
Thr Phe Ala Glu Met Tyr Arg Arg Lys Met Ser Arg Asp Leu Glu Leu
                325                 330                 335 gcc agg ttg aag aag atg gcg aag atg gag agt ggg gag gaa ggg gcc       1056
Ala Arg Leu Lys Lys Met Ala Lys Met Glu Ser Gly Glu Glu Gly Ala
            340                 345                 350 gca gga aag act gct gag gtt act gga gca aag gca tta aat gag att       1104
Ala Gly Lys Thr Ala Glu Val Thr Gly Ala Lys Ala Leu Asn Glu Ile
        355                 360                 365 tta gct taa                                                            1113
Leu Ala
    370

<210> SEQ ID NO 51
<211> LENGTH: 370
<212> TYPE: PRT
<213> ORGANISM: Doritaenopsis hybrid cultivar

<400> SEQUENCE: 51

Met Ala Pro Ile Pro Phe Leu Pro Thr Ala Val Thr Glu Lys Thr Leu
1               5                   10                  15

Arg Ala Ser Phe Val Arg Asp Glu Asp Glu Arg Pro Lys Val Ala Tyr
                20                  25                  30

Asn Glu Phe Ser Asn Gln Ile Pro Val Ile Ser Leu Gln Gly Ile Glu
            35                  40                  45

Glu Asn Gly Asp Gly Gly Arg Ser Glu Ile Cys Arg Ser Ile Val
        50                  55                  60

Ala Ala Cys Glu Asp Trp Gly Ile Phe Gln Ala Val Asp His Gly Val
65                  70                  75                  80

Asp Ala Gly Leu Ile Ala Asp Met Asn Arg Leu Ala Arg Glu Phe Phe
                85                  90                  95

Asp Leu Leu Pro Glu Glu Lys Leu Arg Phe Asp Met Ser Gly Gly Lys
            100                 105                 110

Lys Gly Gly Phe Ile Val Ser Ser His Leu Gln Gly Leu Val Val Gln
        115                 120                 125

Asp Trp Arg Glu Ile Val Thr Tyr Phe Ser Tyr Pro Ile Gly Ser Arg
    130                 135                 140

Asp Tyr Ser Arg Trp Pro Asp Lys Pro Glu Gly Trp Arg Ala Val Val
145                 150                 155                 160

Glu Glu Tyr Ser Ala Lys Leu Met Glu Leu Ala Cys Asn Leu Leu Gly
                165                 170                 175

Val Leu Ser Glu Ala Met Gly Leu Asp Arg Glu Ala Leu Ala Gly Ala
            180                 185                 190

Cys Ile Asp Met Asp Gln Lys Leu Val Val Asn Phe Tyr Pro Lys Cys
        195                 200                 205

Pro Gln Pro Asp Leu Thr Leu Gly Leu Lys Arg His Thr Asp Pro Gly
    210                 215                 220

Thr Ile Thr Leu Leu Leu Gln Asp Gln Val Gly Gly Leu Gln Ala Thr
225                 230                 235                 240
```

```
Lys Asp Asp Gly Lys Thr Trp Ile Thr Val Gln Pro Val Gln Asn Ala
            245                 250                 255
Phe Val Val Asn Leu Gly Asp His Gly His Tyr Leu Ser Asn Gly Arg
            260                 265                 270
Phe Lys Asn Ala Asp His Gln Ala Val Val Asn Ser Asn Tyr Ser Arg
            275                 280                 285
Leu Ser Ile Ala Ala Phe Gln Asn Pro Ala Pro Glu Ala Val Val Tyr
            290                 295                 300
Pro Leu Ala Val Arg Glu Gly Glu Arg Pro Val Met Glu Glu Gly Ile
305                 310                 315                 320
Thr Phe Ala Glu Met Tyr Arg Arg Lys Met Ser Arg Asp Leu Glu Leu
                325                 330                 335
Ala Arg Leu Lys Lys Met Ala Lys Met Glu Ser Gly Glu Glu Gly Ala
            340                 345                 350
Ala Gly Lys Thr Ala Glu Val Thr Gly Ala Lys Ala Leu Asn Glu Ile
            355                 360                 365
Leu Ala
    370
```

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (9)..(9)
<223> OTHER INFORMATION: Inosine
<220> FEATURE:
<221> NAME/KEY: modified_base
<222> LOCATION: (12)..(12)
<223> OTHER INFORMATION: Inosine
<220> FEATURE:
<221> NAME/KEY: modified_base
<222> LOCATION: (15)..(15)
<223> OTHER INFORMATION: a, c, t, g, unknown or other
<220> FEATURE:
<221> NAME/KEY: modified_base
<222> LOCATION: (18)..(18)
<223> OTHER INFORMATION: a, c, t, g, unknown or other

<400> SEQUENCE: 52
ttycaygtng cnacnccnat g                                              21

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (4)..(4)
<223> OTHER INFORMATION: a, c, t, g, unknown or other

<400> SEQUENCE: 53
datngcrtcr tcraacatyt c                                              21

<210> SEQ ID NO 54
<211> LENGTH: 23
<212> TYPE: DNA
<213> ORGANISM: Artificial Sequence
<220> FEATURE:
<223> OTHER INFORMATION: Description of Artificial Sequence: Synthetic

```
            primer
<220> FEATURE:
<221> NAME/KEY: modified_base
<222> LOCATION: (15)..(15)
<223> OTHER INFORMATION: Inosine

<400> SEQUENCE: 54
atgaayttyc arwsnrarga ycc                                              23

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (4)..(4)
<223> OTHER INFORMATION: Inosine
<220> FEATURE:
<221> NAME/KEY: modified_base
<222> LOCATION: (10)..(10)
<223> OTHER INFORMATION: Inosine
<220> FEATURE:
<221> NAME/KEY: modified_base
<222> LOCATION: (13)..(13)
<223> OTHER INFORMATION: a, c, t, g, unknown or other
<220> FEATURE:
<221> NAME/KEY: modified_base
<222> LOCATION: (15)..(15)
<223> OTHER INFORMATION: Inosine
<220> FEATURE:
<221> NAME/KEY: modified_base
<222> LOCATION: (19)..(19)
<223> OTHER INFORMATION: a, c, t, g, unknown or other

<400> SEQUENCE: 55
rcanatrtan ckncnrttng c                                                21

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (12)..(12)
<223> OTHER INFORMATION: a, c, t, g, unknown or other

<400> SEQUENCE: 56
garaaygarg tnathaarcc                                                  20

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (7)..(7)
<223> OTHER INFORMATION: Inosine
<220> FEATURE:
<221> NAME/KEY: modified_base
<222> LOCATION: (13)..(13)
<223> OTHER INFORMATION: a, c, t, g, unknown or other

<400> SEQUENCE: 57
rtcrtcnarr tgnacraayt g                                                21
```

-continued

<210> SEQ ID NO 58
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
ggtcatgcaa aaggtcgggc agcgtaa                                      27

<210> SEQ ID NO 59
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
gtgatcttca catcttccgc aggaacagt                                    29

<210> SEQ ID NO 60
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
atgattcatt aaaaatccga aaaaagacc actacaa                            37

<210> SEQ ID NO 61
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
aaccatgcat aataaagcag atgtgtaaat                                   30

<210> SEQ ID NO 62
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
aaaaaatgga ggatgtgagg aagggtcctg tt                                32

<210> SEQ ID NO 63
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
acatgattca ttaaaaatcc gaaaaaaga cca                                33

<210> SEQ ID NO 64
<211> LENGTH: 1140
<212> TYPE: DNA
<213> ORGANISM: Doritaenopsis hybrid cultivar
<220> FEATURE:
<221> NAME/KEY: CDS
<222> LOCATION: (1)..(1137)
<223> OTHER INFORMATION: Doritaenopsis hybrid cultivar dihydroflavonol 4-reductase ( PhDFR )

<400> SEQUENCE: 64

```
atg gag gat gtg agg aag ggt cct gtt gtg gtg acg gga gcc agc ggg      48
Met Glu Asp Val Arg Lys Gly Pro Val Val Val Thr Gly Ala Ser Gly
1               5                   10                  15 tac gtg ggt tca tgg ctg gtt atg aag ctt ctt cga aag ggt tat gag      96
Tyr Val Gly Ser Trp Leu Val Met Lys Leu Leu Arg Lys Gly Tyr Glu
            20                  25                  30 gtc agg gct aca gtc aga gat cca aca aat tct aaa aaa gtg aag ccg     144
Val Arg Ala Thr Val Arg Asp Pro Thr Asn Ser Lys Lys Val Lys Pro
        35                  40                  45 ttg ttg gat ctt ccg ggc tcg aat gaa ctg ctc agc ata tgg aaa gca     192
Leu Leu Asp Leu Pro Gly Ser Asn Glu Leu Leu Ser Ile Trp Lys Ala
    50                  55                  60 gat cta aat gac att gaa ggg agc ttc gat gag gtg ata cgt ggt tgt     240
Asp Leu Asn Asp Ile Glu Gly Ser Phe Asp Glu Val Ile Arg Gly Cys
65                  70                  75                  80 gtt ggg gtg ttc cat gtc gct act ccc atg aat ttt caa tcc aaa gac     288
Val Gly Val Phe His Val Ala Thr Pro Met Asn Phe Gln Ser Lys Asp
                85                  90                  95 cct gag aac gaa gtg ata caa ccg gca atc aac ggt ttg ctg agc atc     336
Pro Glu Asn Glu Val Ile Gln Pro Ala Ile Asn Gly Leu Leu Ser Ile
            100                 105                 110 ctg agg tca tgc aaa agg tcg ggc agc gta agg cgc gtg atc ttc aca     384
Leu Arg Ser Cys Lys Arg Ser Gly Ser Val Arg Arg Val Ile Phe Thr
        115                 120                 125 tct tcc gca gga aca gtc aac gtg gag gaa cgc cga gca ccg gtg tac     432
Ser Ser Ala Gly Thr Val Asn Val Glu Glu Arg Arg Ala Pro Val Tyr
    130                 135                 140 gac gag agc tcc tgg agc gac ctc gat ttc atc acc cgt gtc aaa atg     480
Asp Glu Ser Ser Trp Ser Asp Leu Asp Phe Ile Thr Arg Val Lys Met
145                 150                 155                 160 acc ggt tgg atg tac ttc gta tca aaa aca ctt gcg gag aag gct gct     528
Thr Gly Trp Met Tyr Phe Val Ser Lys Thr Leu Ala Glu Lys Ala Ala
                165                 170                 175 tgg gag ttt gtg aaa gaa aat gac gtt gat ttt ata gcc ata att ccc     576
Trp Glu Phe Val Lys Glu Asn Asp Val Asp Phe Ile Ala Ile Ile Pro
            180                 185                 190 act ttg gtg gtg ggt tcc ttc ata aca gat gag atg ccg cca agt ttg     624
Thr Leu Val Val Gly Ser Phe Ile Thr Asp Glu Met Pro Pro Ser Leu
        195                 200                 205 acc act gca ttt tca tta att aca gga aat gaa gct cat tac tcg ata     672
Thr Thr Ala Phe Ser Leu Ile Thr Gly Asn Glu Ala His Tyr Ser Ile
    210                 215                 220 ata aag caa gct caa ttt gtt cat ttg gat gac tta tgt gat gct cat     720
Ile Lys Gln Ala Gln Phe Val His Leu Asp Asp Leu Cys Asp Ala His
225                 230                 235                 240 att ttc ctt ttc gaa cat ccc gaa gca aat ggt agg tac att tgt tct     768
Ile Phe Leu Phe Glu His Pro Glu Ala Asn Gly Arg Tyr Ile Cys Ser
                245                 250                 255 tca cat gat tcg aca att tat gac ttg gca aaa atg ctg aag aag aga     816
Ser His Asp Ser Thr Ile Tyr Asp Leu Ala Lys Met Leu Lys Lys Arg
            260                 265                 270
```

```
tat gcc aca tat gcc ata cct caa gag ttt aaa gat att gat cca aat    864
Tyr Ala Thr Tyr Ala Ile Pro Gln Glu Phe Lys Asp Ile Asp Pro Asn
        275                 280                 285 att aag aga gtg agt ttc tct tct aag aag ttc atg gac ttg ggg ttc    912
Ile Lys Arg Val Ser Phe Ser Ser Lys Lys Phe Met Asp Leu Gly Phe
    290                 295                 300 aag tac aag tac act att gag gag atg ttt gat gat gct att aag acc    960
Lys Tyr Lys Tyr Thr Ile Glu Glu Met Phe Asp Asp Ala Ile Lys Thr
305                 310                 315                 320 tgc agg gaa aag aat ctc tta ccg ccc aac act gag gaa cca gcc tta   1008
Cys Arg Glu Lys Asn Leu Leu Pro Pro Asn Thr Glu Glu Pro Ala Leu
            325                 330                 335 ctt gcc gaa aag tac gaa gaa atg aaa gaa caa ttg cag tta agt gaa   1056
Leu Ala Glu Lys Tyr Glu Glu Met Lys Glu Gln Leu Gln Leu Ser Glu
        340                 345                 350 aga aga atg aga agt ttg aaa att ctt tat gtt atc ctt tta ttt aca   1104
Arg Arg Met Arg Ser Leu Lys Ile Leu Tyr Val Ile Leu Leu Phe Thr
    355                 360                 365 cat ctg ctt tat tat gca tgg tta tat ctt gac tga                   1140
His Leu Leu Tyr Tyr Ala Trp Leu Tyr Leu Asp
370                 375
```

<210> SEQ ID NO 65
<211> LENGTH: 379
<212> TYPE: PRT
<213> ORGANISM: Doritaenopsis hybrid cultivar

<400> SEQUENCE: 65

```
Met Glu Asp Val Arg Lys Gly Pro Val Val Thr Gly Ala Ser Gly
1               5                   10                  15

Tyr Val Gly Ser Trp Leu Val Met Lys Leu Leu Arg Lys Gly Tyr Glu
                20                  25                  30

Val Arg Ala Thr Val Arg Asp Pro Thr Asn Ser Lys Lys Val Lys Pro
            35                  40                  45

Leu Leu Asp Leu Pro Gly Ser Asn Glu Leu Leu Ser Ile Trp Lys Ala
        50                  55                  60

Asp Leu Asn Asp Ile Glu Gly Ser Phe Asp Glu Val Ile Arg Gly Cys
65                  70                  75                  80

Val Gly Val Phe His Val Ala Thr Pro Met Asn Phe Gln Ser Lys Asp
                85                  90                  95

Pro Glu Asn Glu Val Ile Gln Pro Ala Ile Asn Gly Leu Leu Ser Ile
            100                 105                 110

Leu Arg Ser Cys Lys Arg Ser Gly Ser Val Arg Arg Val Ile Phe Thr
        115                 120                 125

Ser Ser Ala Gly Thr Val Asn Val Glu Glu Arg Arg Ala Pro Val Tyr
    130                 135                 140

Asp Glu Ser Ser Trp Ser Asp Leu Asp Phe Ile Thr Arg Val Lys Met
145                 150                 155                 160

Thr Gly Trp Met Tyr Phe Val Ser Lys Thr Leu Ala Glu Lys Ala Ala
                165                 170                 175

Trp Glu Phe Val Lys Glu Asn Asp Val Asp Phe Ile Ala Ile Ile Pro
            180                 185                 190

Thr Leu Val Val Gly Ser Phe Ile Thr Asp Glu Met Pro Pro Ser Leu
        195                 200                 205

Thr Thr Ala Phe Ser Leu Ile Thr Gly Asn Glu Ala His Tyr Ser Ile
    210                 215                 220

Ile Lys Gln Ala Gln Phe Val His Leu Asp Asp Leu Cys Asp Ala His
225                 230                 235                 240
```

```
Ile Phe Leu Phe Glu His Pro Glu Ala Asn Gly Arg Tyr Ile Cys Ser
                245                 250                 255

Ser His Asp Ser Thr Ile Tyr Asp Leu Ala Lys Met Leu Lys Lys Arg
            260                 265                 270

Tyr Ala Thr Tyr Ala Ile Pro Gln Glu Phe Lys Asp Ile Asp Pro Asn
        275                 280                 285

Ile Lys Arg Val Ser Phe Ser Ser Lys Lys Phe Met Asp Leu Gly Phe
    290                 295                 300

Lys Tyr Lys Tyr Thr Ile Glu Glu Met Phe Asp Asp Ala Ile Lys Thr
305                 310                 315                 320

Cys Arg Glu Lys Asn Leu Leu Pro Pro Asn Thr Glu Glu Pro Ala Leu
                325                 330                 335

Leu Ala Glu Lys Tyr Glu Glu Met Lys Glu Gln Leu Gln Leu Ser Glu
            340                 345                 350

Arg Arg Met Arg Ser Leu Lys Ile Leu Tyr Val Ile Leu Leu Phe Thr
        355                 360                 365

His Leu Leu Tyr Tyr Ala Trp Leu Tyr Leu Asp
    370                 375

<210> SEQ ID NO 66
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (2)..(2)
<223> OTHER INFORMATION: Inosine
<220> FEATURE:
<221> NAME/KEY: modified_base
<222> LOCATION: (14)..(14)
<223> OTHER INFORMATION: Inosine
<220> FEATURE:
<221> NAME/KEY: modified_base
<222> LOCATION: (23)..(23)
<223> OTHER INFORMATION: Inosine
<220> FEATURE:
<221> NAME/KEY: modified_base
<222> LOCATION: (26)..(26)
<223> OTHER INFORMATION: Inosine

<400> SEQUENCE: 66
tncarggbta yggnagyarr ytngcnrmya                                      30

<210> SEQ ID NO 67
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (12)..(12)
<223> OTHER INFORMATION: Inosine
<220> FEATURE:
<221> NAME/KEY: modified_base
<222> LOCATION: (15)..(15)
<223> OTHER INFORMATION: Inosine
<220> FEATURE:
<221> NAME/KEY: modified_base
<222> LOCATION: (21)..(21)
<223> OTHER INFORMATION: Inosine

<400> SEQUENCE: 67
```
ggytcrcara anaynrccca ngada                                         25

<210> SEQ ID NO 68
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
gcccacaccg acgtcagctc cctctcct                                      28

<210> SEQ ID NO 69
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
cgtcggggat gcgctcgaga tcctcagc                                      28

<210> SEQ ID NO 70
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
agtccgcggg ttcagtcggc cagatggt                                      28

<210> SEQ ID NO 71
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
ccgtcttctc cggcgggtag acgaggtg                                      28

<210> SEQ ID NO 72
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
atggccacca aagcaatccc acc                                           23

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
tcaatccaca ggcgccttct                                               20

<210> SEQ ID NO 74
<211> LENGTH: 1083
<212> TYPE: DNA
<213> ORGANISM: Doritaenopsis hybrid cultivar
<220> FEATURE:
<221> NAME/KEY: CDS
<222> LOCATION: (1)..(1080)
<223> OTHER INFORMATION: Doritaenopsis hybrid cultivar anthocyanidin synthase ( PhANS 1 )

<400> SEQUENCE: 74

```
atg gcc acc aaa gca atc cca cct act cca aga gtg gag atc ctc gca        48
Met Ala Thr Lys Ala Ile Pro Pro Thr Pro Arg Val Glu Ile Leu Ala
1               5                   10                  15 aac agc ggc ctc agc ttc atc ccc gcc gag ttc gtc cgc cca caa tct        96
Asn Ser Gly Leu Ser Phe Ile Pro Ala Glu Phe Val Arg Pro Gln Ser
            20                  25                  30 gaa cgc caa cac ctc caa gac tcc ctc aac aag aac ccc tgc ggt gtt       144
Glu Arg Gln His Leu Gln Asp Ser Leu Asn Lys Asn Pro Cys Gly Val
        35                  40                  45 gag atc cca atc gtg gat ctc ggg ggg ttc tca tca gag gaa ggg cgg       192
Glu Ile Pro Ile Val Asp Leu Gly Gly Phe Ser Ser Glu Glu Gly Arg
    50                  55                  60 cgg cgg cgg tgc gtg gag gag gtg atg gca gct gca gag gag tgg ggg       240
Arg Arg Arg Cys Val Glu Glu Val Met Ala Ala Ala Glu Glu Trp Gly
65                  70                  75                  80 gtg atg ttc ctc gtg aac cac ggt gtg ccg gag gag ctc att gag cgg       288
Val Met Phe Leu Val Asn His Gly Val Pro Glu Glu Leu Ile Glu Arg
                85                  90                  95 ctg cag gcg acg ggg aag ggg ttc ttc gaa ttg ccg gtg gac gag aag       336
Leu Gln Ala Thr Gly Lys Gly Phe Phe Glu Leu Pro Val Asp Glu Lys
            100                 105                 110 gag aag tat gct aat gat cag tca agg gga cag ata cag ggc tat ggg       384
Glu Lys Tyr Ala Asn Asp Gln Ser Arg Gly Gln Ile Gln Gly Tyr Gly
        115                 120                 125 agc aag cta gca aat aat gaa aac ggt ata ctt gag tgg cag gat tac       432
Ser Lys Leu Ala Asn Asn Glu Asn Gly Ile Leu Glu Trp Gln Asp Tyr
    130                 135                 140 ttt ttt cac ctc gtc tac ccg ccg gag aag acg gac ctc acc atc tgg       480
Phe Phe His Leu Val Tyr Pro Pro Glu Lys Thr Asp Leu Thr Ile Trp
145                 150                 155                 160 ccg act gaa ccc gcg gac tac att gcg acc aca acc tcg ttc gcc aag       528
Pro Thr Glu Pro Ala Asp Tyr Ile Ala Thr Thr Thr Ser Phe Ala Lys
                165                 170                 175 gag ctc cga acc cta gcc tca aaa atg ttc tcc ata ctc tcc ctc ggt       576
Glu Leu Arg Thr Leu Ala Ser Lys Met Phe Ser Ile Leu Ser Leu Gly
            180                 185                 190 ctc ggc ctc gac caa aac aag ctc gaa gct gag ctc ggc ggc caa gac       624
Leu Gly Leu Asp Gln Asn Lys Leu Glu Ala Glu Leu Gly Gly Gln Asp
        195                 200                 205 gac ctc ctc ctc cag ctt aag atc aat tac tac ccg ccc tgc ccg cag       672
Asp Leu Leu Leu Gln Leu Lys Ile Asn Tyr Tyr Pro Pro Cys Pro Gln
    210                 215                 220 ccg gag ctg gcc ctc ggc gtc gag gcc cac acc gac gtc agc tcc ctc       720
Pro Glu Leu Ala Leu Gly Val Glu Ala His Thr Asp Val Ser Ser Leu
225                 230                 235                 240 tcc ttc atc ctt cac aac ggg atc ccc ggc ctc cag gtc ttc aag aac       768
Ser Phe Ile Leu His Asn Gly Ile Pro Gly Leu Gln Val Phe Lys Asn
                245                 250                 255 ggc gcc ggc tgg atc acc gct ccc ctc gtc cca aac tcg atc atc gtt       816
Gly Ala Gly Trp Ile Thr Ala Pro Leu Val Pro Asn Ser Ile Ile Val
            260                 265                 270
```

```
cac gtc ggg gat gcg ctc gag atc ctc agc aat ggg agg tgc cac agc      864
His Val Gly Asp Ala Leu Glu Ile Leu Ser Asn Gly Arg Cys His Ser
        275                 280                 285 gtt ctt cac cga gga ctt gtt act aag gaa aat gtt cgg atc tcg tgg      912
Val Leu His Arg Gly Leu Val Thr Lys Glu Asn Val Arg Ile Ser Trp
    290                 295                 300 gcg gtt ttc tgc gag ccg ccg agg gag aag gtg gtt ctt cgg ccg ctg      960
Ala Val Phe Cys Glu Pro Pro Arg Glu Lys Val Val Leu Arg Pro Leu
305                 310                 315                 320 ctg gag ttg att ggg aag ggg gag gtg gcg agg ttt gag ccg cgg act     1008
Leu Glu Leu Ile Gly Lys Gly Glu Val Ala Arg Phe Glu Pro Arg Thr
                325                 330                 335 ttt gcg gag cat ttg gag agg aag ctg ttc aag ccg agg gtg gag ggt     1056
Phe Ala Glu His Leu Glu Arg Lys Leu Phe Lys Pro Arg Val Glu Gly
            340                 345                 350 tgc ggg gag aag gcg cct gtg gat tga                                 1083
Cys Gly Glu Lys Ala Pro Val Asp
        355                 360

<210> SEQ ID NO 75
<211> LENGTH: 360
<212> TYPE: PRT
<213> ORGANISM: Doritaenopsis hybrid cultivar

<400> SEQUENCE: 75

Met Ala Thr Lys Ala Ile Pro Pro Thr Pro Arg Val Glu Ile Leu Ala
1               5                   10                  15

Asn Ser Gly Leu Ser Phe Ile Pro Ala Glu Phe Val Arg Pro Gln Ser
            20                  25                  30

Glu Arg Gln His Leu Gln Asp Ser Leu Asn Lys Asn Pro Cys Gly Val
        35                  40                  45

Glu Ile Pro Ile Val Asp Leu Gly Gly Phe Ser Ser Glu Glu Gly Arg
    50                  55                  60

Arg Arg Arg Cys Val Glu Val Met Ala Ala Glu Glu Trp Gly
65                  70                  75                  80

Val Met Phe Leu Val Asn His Gly Val Pro Glu Glu Leu Ile Glu Arg
                85                  90                  95

Leu Gln Ala Thr Gly Lys Gly Phe Phe Glu Leu Pro Val Asp Glu Lys
            100                 105                 110

Glu Lys Tyr Ala Asn Asp Gln Ser Arg Gly Gln Ile Gln Gly Tyr Gly
        115                 120                 125

Ser Lys Leu Ala Asn Asn Glu Asn Gly Ile Leu Glu Trp Gln Asp Tyr
    130                 135                 140

Phe Phe His Leu Val Tyr Pro Pro Glu Lys Thr Asp Leu Thr Ile Trp
145                 150                 155                 160

Pro Thr Glu Pro Ala Asp Tyr Ile Ala Thr Thr Thr Ser Phe Ala Lys
                165                 170                 175

Glu Leu Arg Thr Leu Ala Ser Lys Met Phe Ser Ile Leu Ser Leu Gly
            180                 185                 190

Leu Gly Leu Asp Gln Asn Lys Leu Glu Ala Glu Leu Gly Gly Gln Asp
        195                 200                 205

Asp Leu Leu Leu Gln Leu Lys Ile Asn Tyr Tyr Pro Pro Cys Pro Gln
    210                 215                 220

Pro Glu Leu Ala Leu Gly Val Glu Ala His Thr Asp Val Ser Ser Leu
225                 230                 235                 240

Ser Phe Ile Leu His Asn Gly Ile Pro Gly Leu Gln Val Phe Lys Asn
                245                 250                 255
```

```
Gly Ala Gly Trp Ile Thr Ala Pro Leu Val Pro Asn Ser Ile Ile Val
            260                 265                 270

His Val Gly Asp Ala Leu Glu Ile Leu Ser Asn Gly Arg Cys His Ser
        275                 280                 285

Val Leu His Arg Gly Leu Val Thr Lys Glu Asn Val Arg Ile Ser Trp
    290                 295                 300

Ala Val Phe Cys Glu Pro Pro Arg Glu Lys Val Val Leu Arg Pro Leu
305                 310                 315                 320

Leu Glu Leu Ile Gly Lys Gly Glu Val Ala Arg Phe Glu Pro Arg Thr
                325                 330                 335

Phe Ala Glu His Leu Glu Arg Lys Leu Phe Lys Pro Arg Val Glu Gly
            340                 345                 350

Cys Gly Glu Lys Ala Pro Val Asp
        355                 360

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
atggaagagg attctccggc                                                 20

<210> SEQ ID NO 77
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
ctattggcct tcttttgaac aacaaa                                          26

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
atggtgattc aagcaaccac a                                               21

<210> SEQ ID NO 79
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
ctagttttgc atcacttcgt ctttat                                          26

<210> SEQ ID NO 80
<211> LENGTH: 24
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 80
atgagcatgg aagtagtagt acca                                          24

<210> SEQ ID NO 81
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
ctattctatc ttatgttctc catgg                                         25

<210> SEQ ID NO 82
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
atggtttctc cagcatctcc ga                                            22

<210> SEQ ID NO 83
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
tcactcaaca ctcttatcat catgctc                                       27

<210> SEQ ID NO 84
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
gaaaccacct gtttgttcaa ga                                            22

<210> SEQ ID NO 85
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
tcaattggtt ataaaggaag aagc                                          24

<210> SEQ ID NO 86
<211> LENGTH: 36
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 86
gtaacatgtc gagcgcttgc gttcttttca tactcg                                    36

<210> SEQ ID NO 87
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
cgagtatgaa aagaacgcaa gcgctcgaca tgttac                                    36
```